United States Patent
Bourque et al.

(10) Patent No.: US 10,758,252 B2
(45) Date of Patent: Sep. 1, 2020

(54) RETRO GUIDEWIRE REAMER

(71) Applicant: Smith & Nephew, Inc., Memphis, TN (US)

(72) Inventors: Bernard J. Bourque, Rehoboth, MA (US); David J. Callaghan, Waltham, MA (US); Michael C. Ferragamo, Foster, RI (US)

(73) Assignee: Smith & Nephew, Inc., Memphis, TN (US)

( * ) Notice: Subject to any disclaimer, the term of this patent is extended or adjusted under 35 U.S.C. 154(b) by 166 days.

(21) Appl. No.: 16/152,483

(22) Filed: Oct. 5, 2018

(65) Prior Publication Data

US 2019/0038299 A1 Feb. 7, 2019

Related U.S. Application Data

(62) Division of application No. 14/198,900, filed on Mar. 6, 2014, now Pat. No. 10,105,150.

(Continued)

(51) Int. Cl.
*A61B 17/32* (2006.01)
*A61B 17/16* (2006.01)
(Continued)

(52) U.S. Cl.
CPC ...... *A61B 17/1714* (2013.01); *A61B 17/1615* (2013.01); *A61B 17/1617* (2013.01);
(Continued)

(58) Field of Classification Search
CPC ............ A61B 17/1714; A61B 17/1615; A61B 17/1617; A61B 17/1631; A61B 17/1697;
(Continued)

(56) References Cited

U.S. PATENT DOCUMENTS

| 5,591,170 | A | * | 1/1997 | Spievack | ............. | A61B 17/151 |
| | | | | | | 30/122 |
| 6,740,090 | B1 | * | 5/2004 | Cragg | ................... | A61B 17/70 |
| | | | | | | 606/79 |

OTHER PUBLICATIONS

Chinese Application No. 201380072359.3 Fourth Office Action dated Oct. 15, 2018.

(Continued)

*Primary Examiner* — Jessica Weiss
(74) *Attorney, Agent, or Firm* — Burns & Levinson, LLP; Joseph M. Maraia

(57) ABSTRACT

A retro guidewire reamer includes a cutting member, and a mechanism for moving the cutting member from a closed position to a deployed position in a single manual motion. Once a desired size of a bone tunnel is established, a surgeon uses the reamer to create a primary bone tunnel over a guidewire from the outside in. The surgeon retracts the guidewire, and activates the mechanism to deploy the cutting member within the bone joint to conform to the size of a tendon graft. The surgeon uses the deployed cutting member to create a counter bore through the bone in a retrograde manner. Once the counter bore is drilled, the surgeon activates the mechanism to close the cutting member, allowing the reamer to be withdrawn through the primary tunnel. The retro guidewire reamer can be used to provide more accurate bone tunnel placement during ligament reconstruction surgery.

9 Claims, 42 Drawing Sheets

Related U.S. Application Data

(60) Provisional application No. 61/776,896, filed on Mar. 12, 2013, provisional application No. 61/805,578, filed on Mar. 27, 2013, provisional application No. 61/858,800, filed on Jul. 26, 2013.

(51) Int. Cl.
*A61B 17/17* (2006.01)
*A61B 90/00* (2016.01)

(52) U.S. Cl.
CPC ...... *A61B 17/1631* (2013.01); *A61B 17/1697* (2013.01); *A61B 17/1622* (2013.01); *A61B 17/1624* (2013.01); *A61B 17/1633* (2013.01); *A61B 17/1675* (2013.01); *A61B 2017/1602* (2013.01); *A61B 2090/036* (2016.02)

(58) Field of Classification Search
CPC ............ A61B 17/1622; A61B 17/1624; A61B 17/1633; A61B 17/1675; A61B 2017/1602; A61B 2090/036
USPC .................................................... 606/79–85
See application file for complete search history.

(56) References Cited

OTHER PUBLICATIONS

Chinese Application No. 201380072359.3 Text of Fourth Office Action.
European Examination Report Application No. 13811705.6-122 dated Mar. 19, 2019.

* cited by examiner

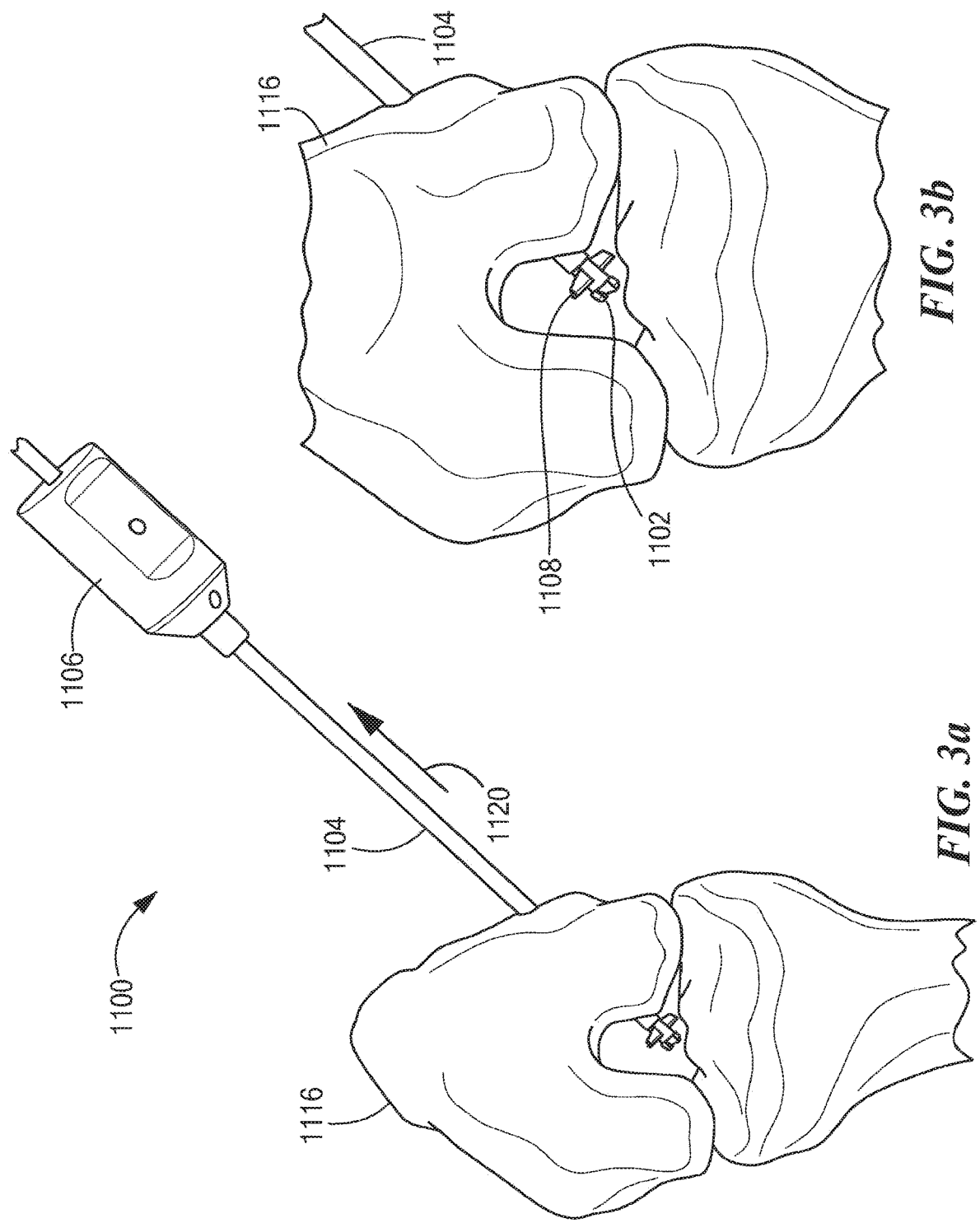

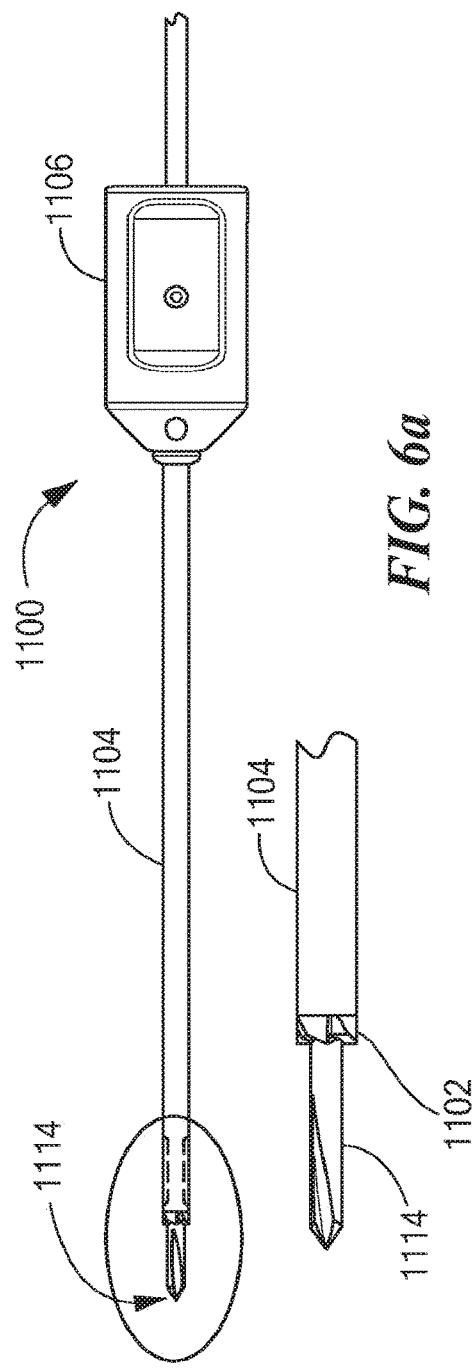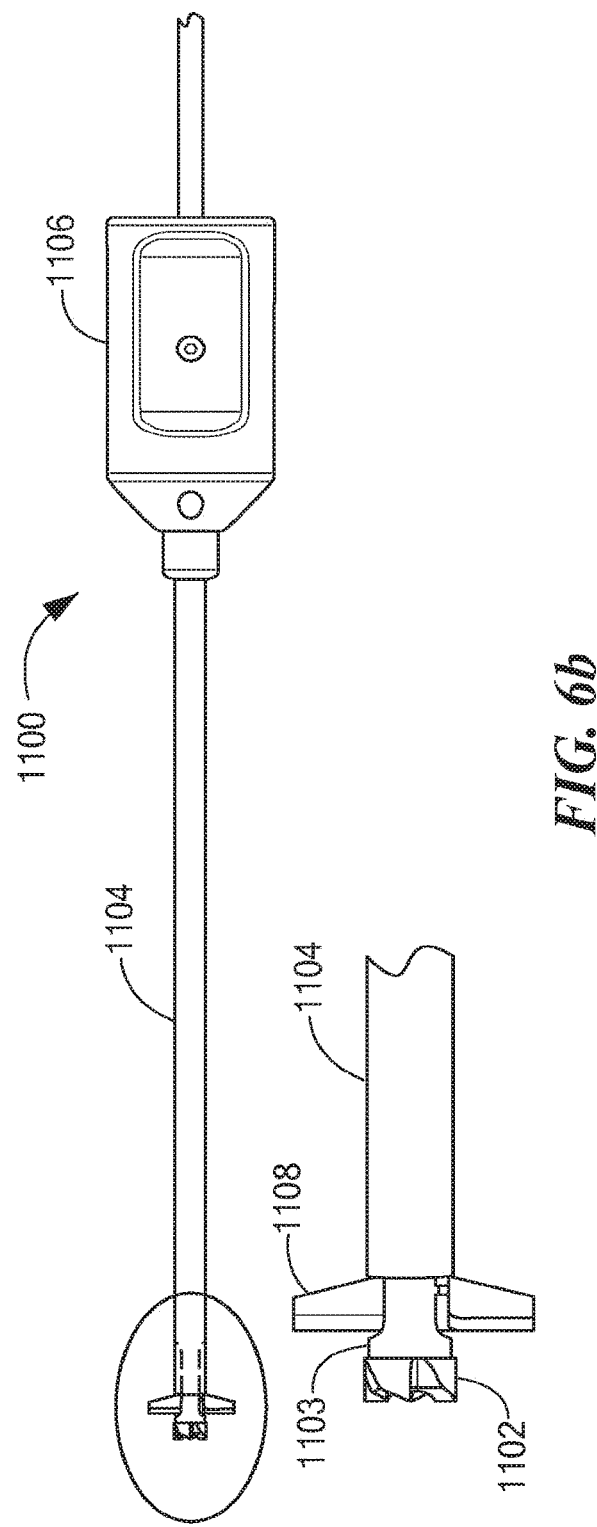
FIG. 6a
FIG. 6b

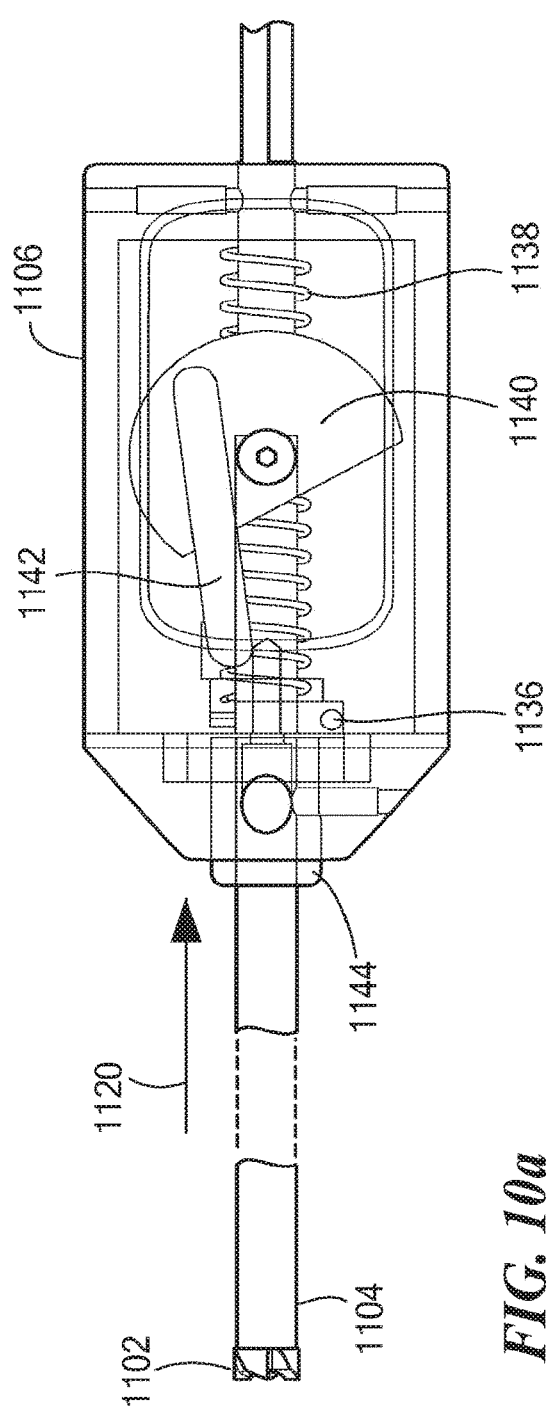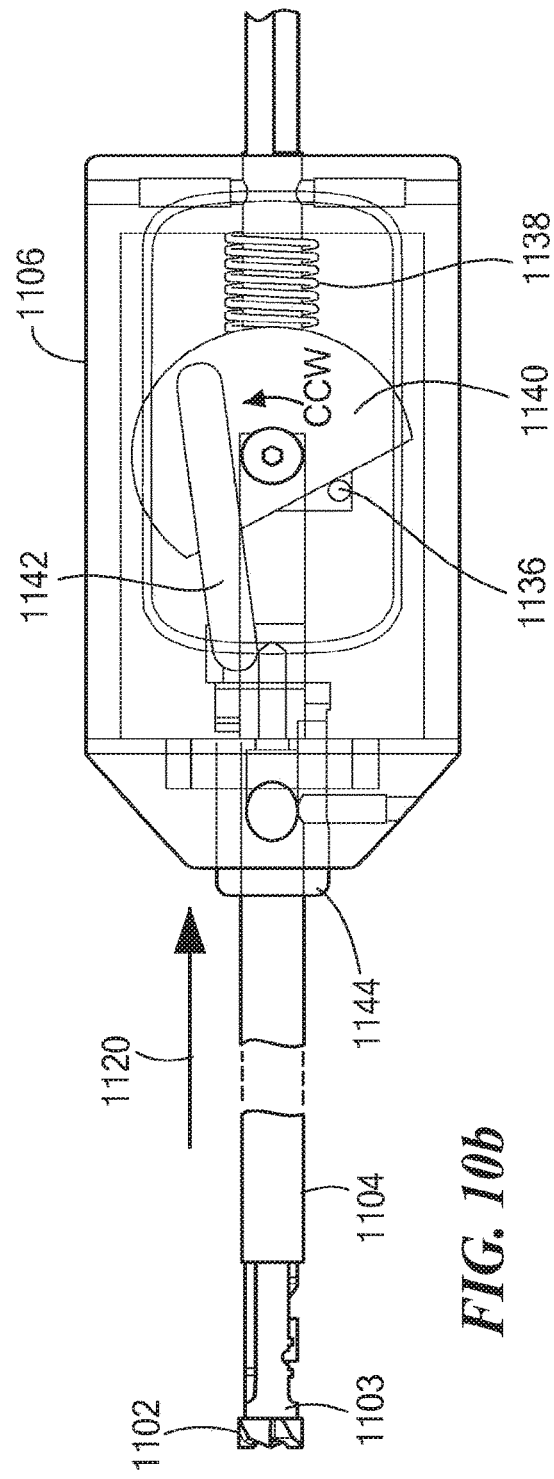
FIG. 10a
FIG. 10b

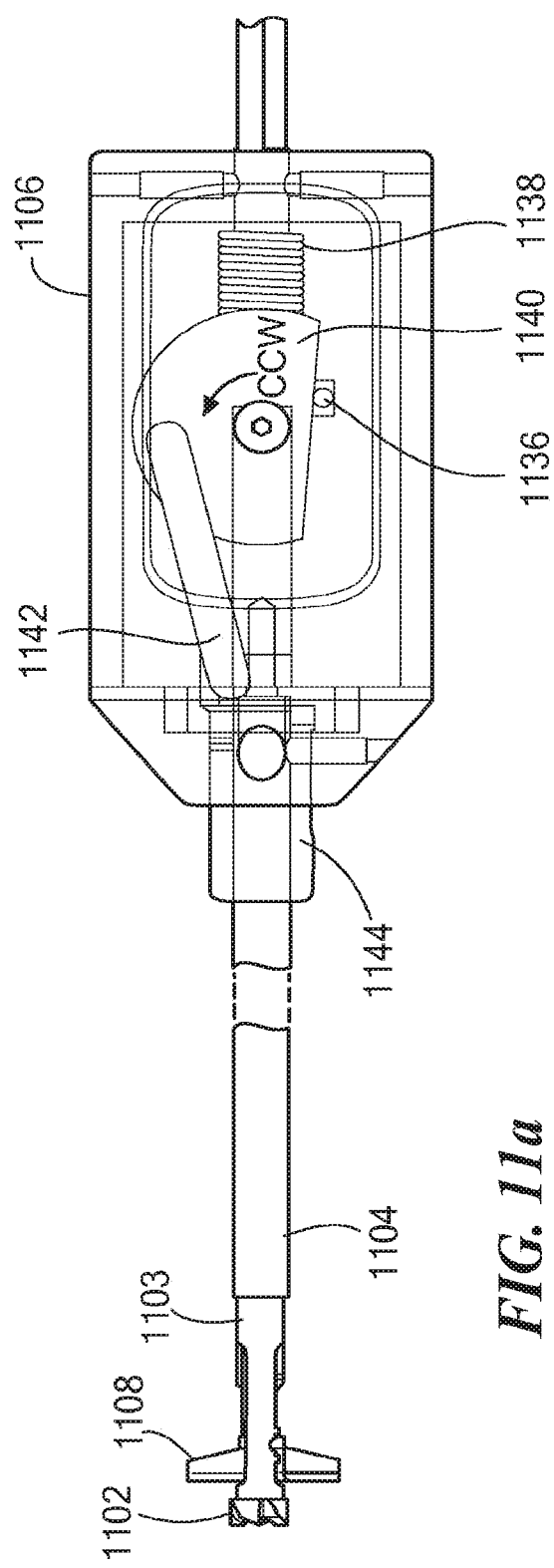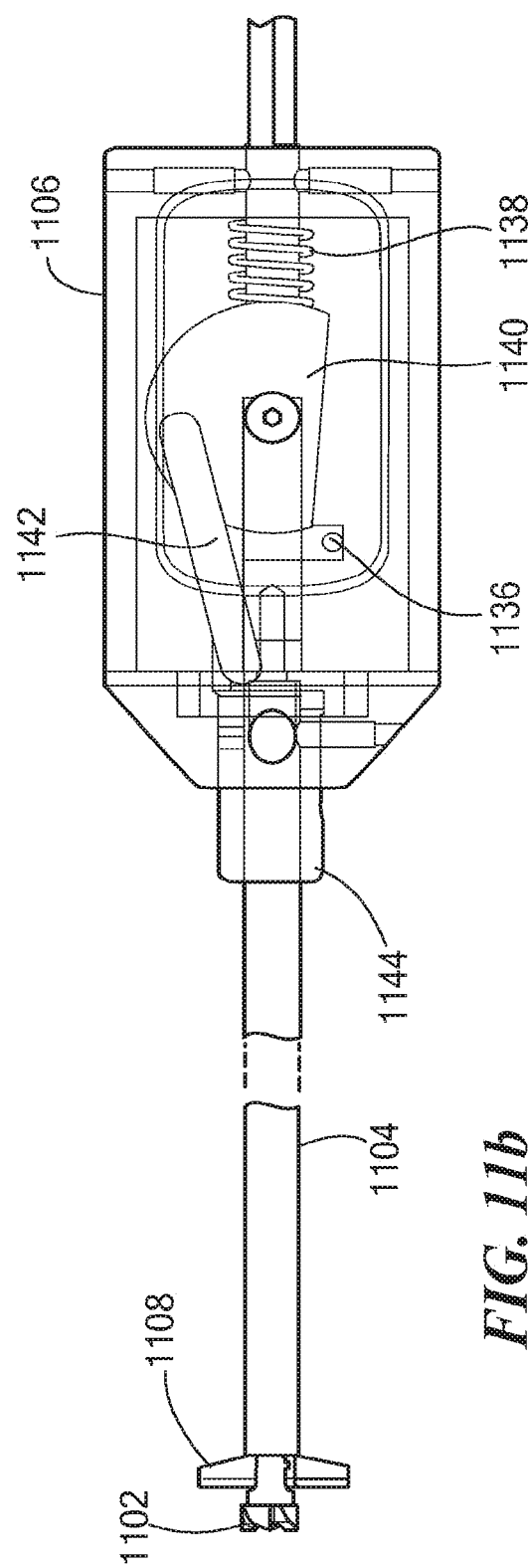
FIG. 11a
FIG. 11b

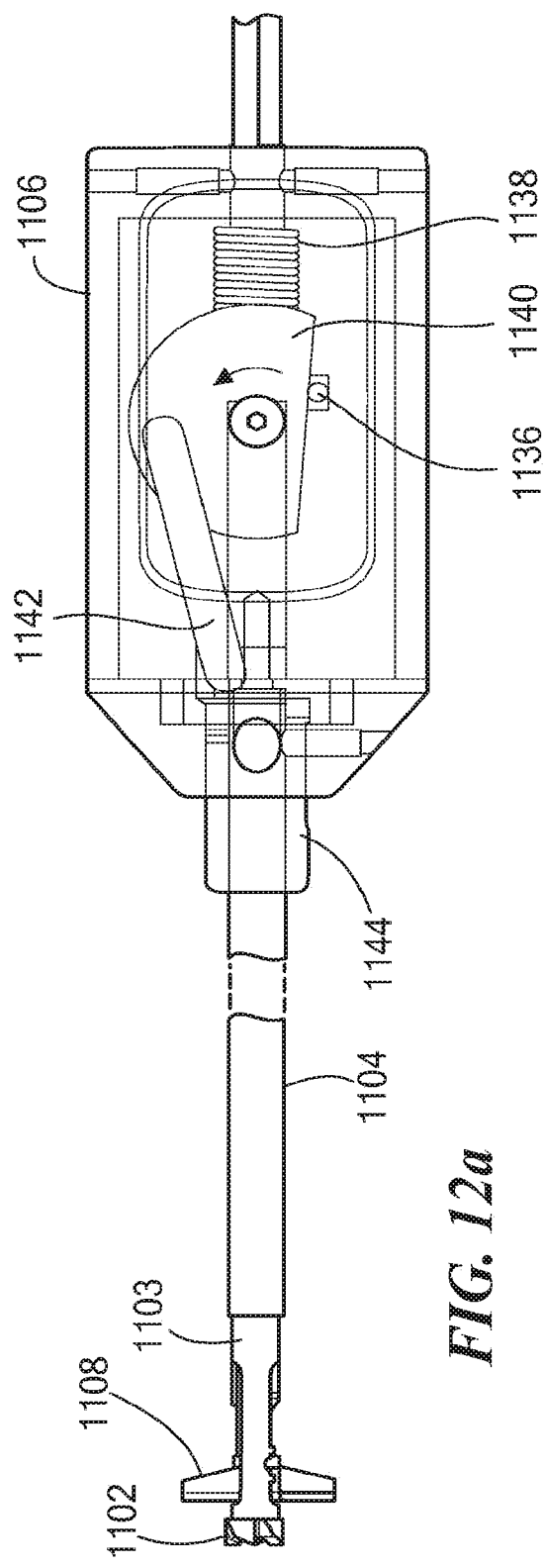
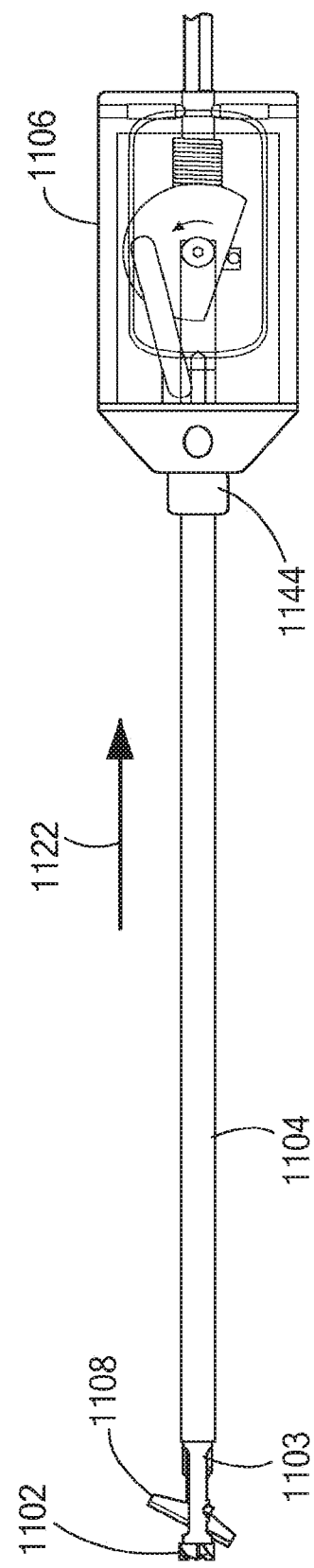
FIG. 12a
FIG. 12b

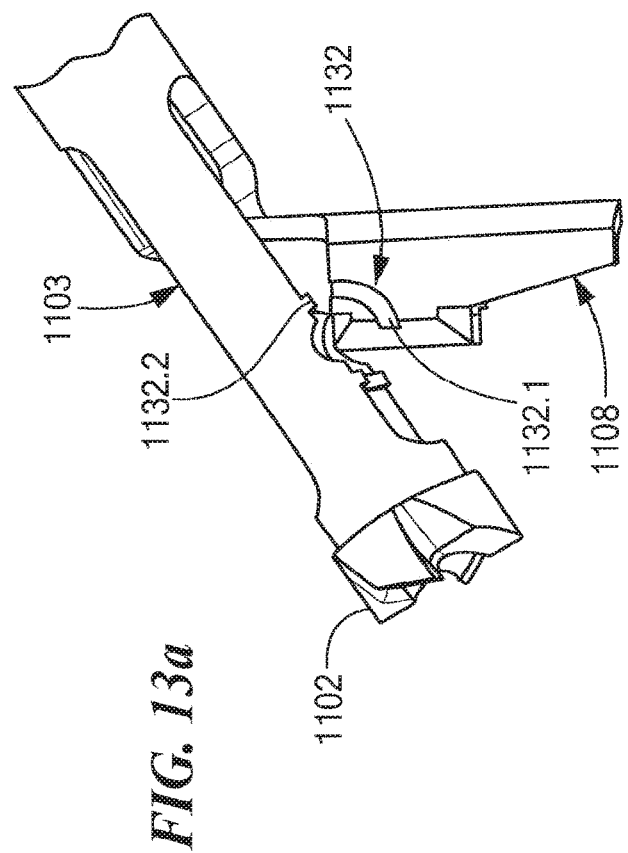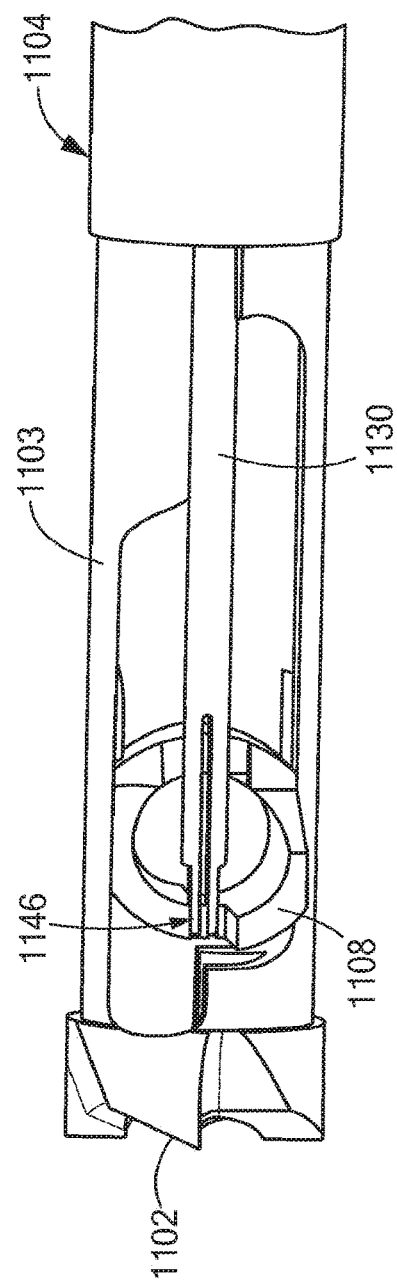

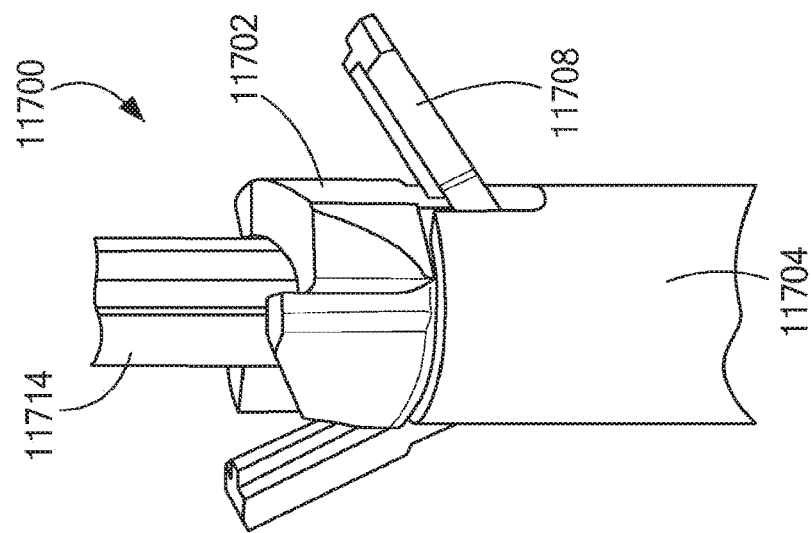
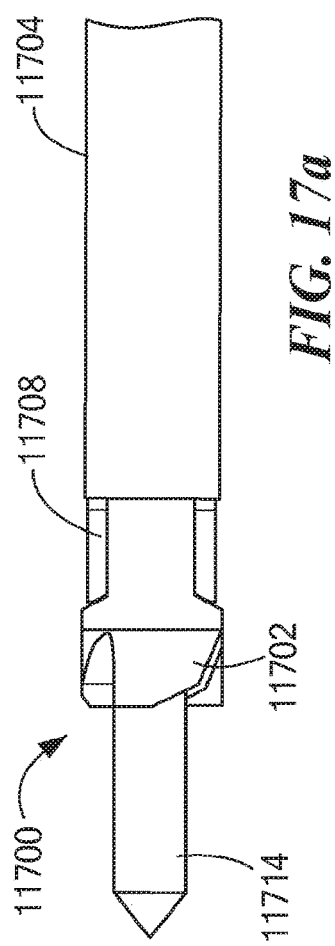
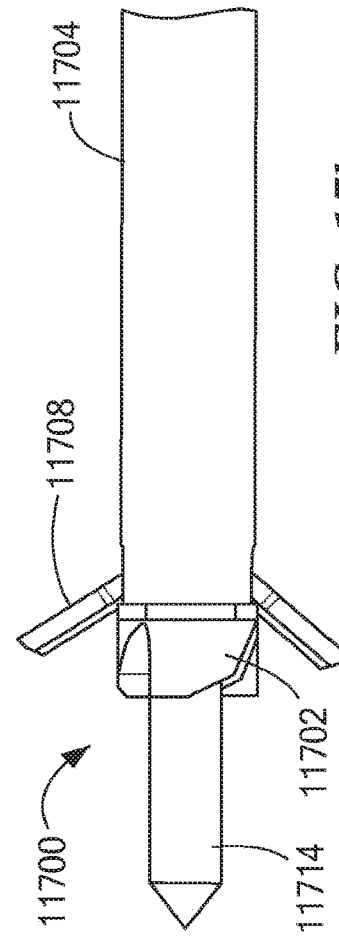
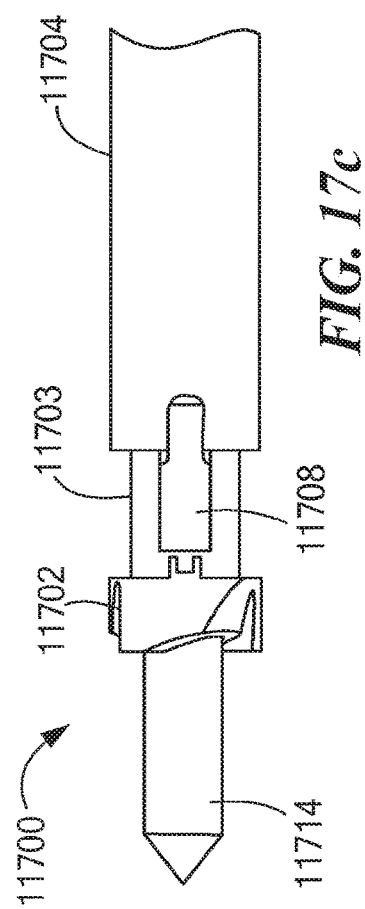

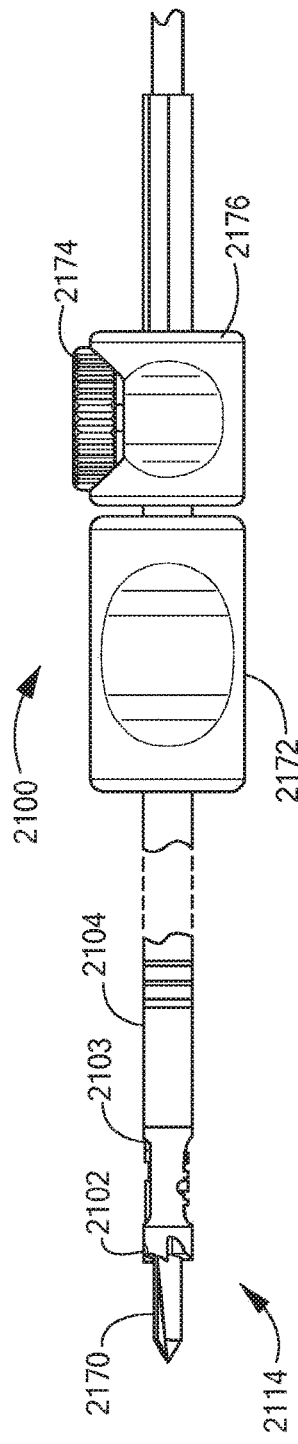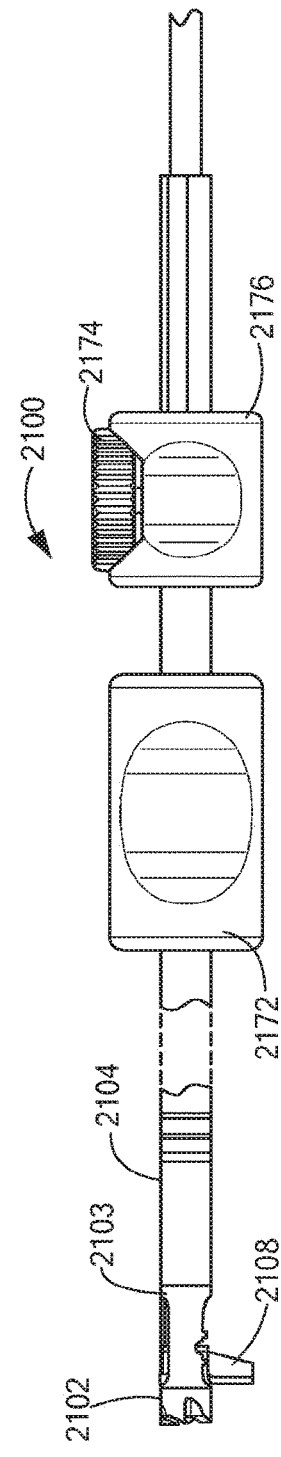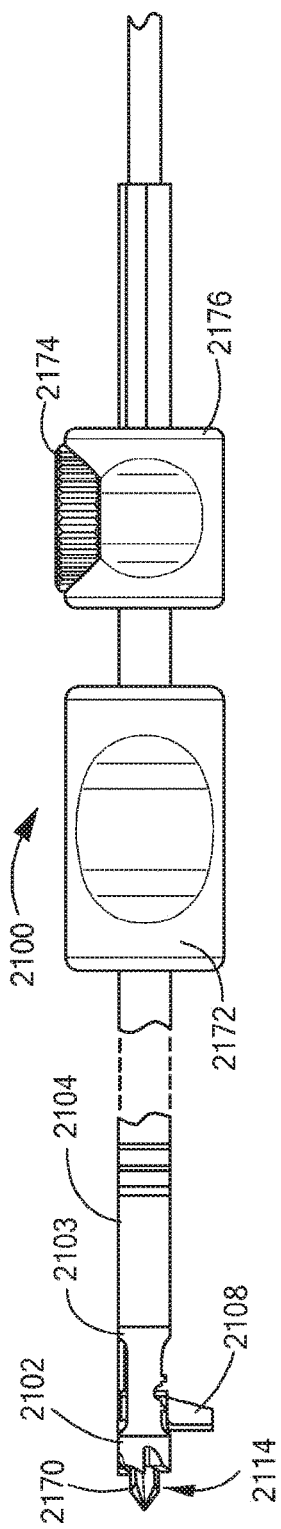
FIG. 22a
FIG. 22b
FIG. 22c

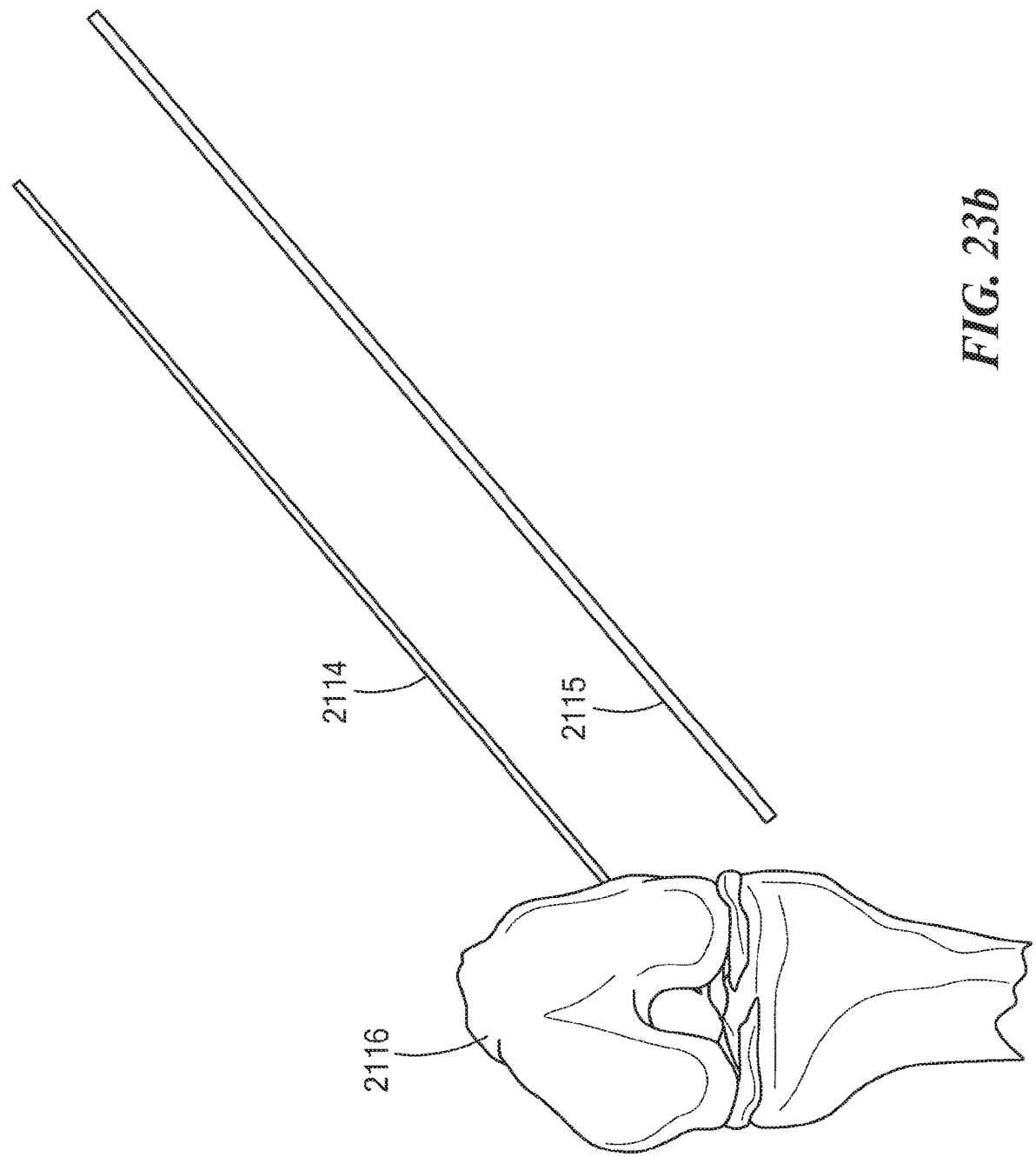

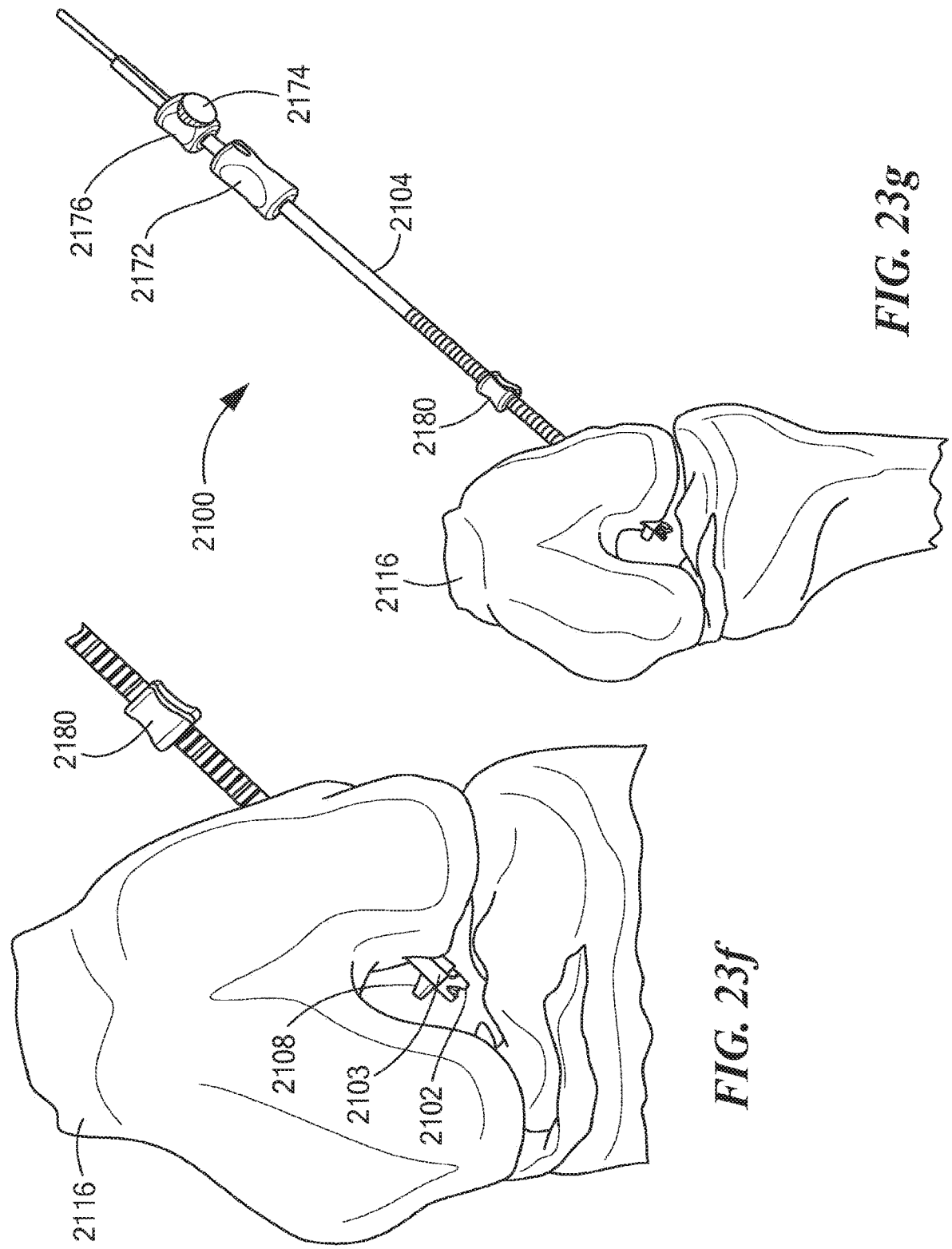

RETRO GUIDEWIRE REAMER

CROSS REFERENCE TO RELATED APPLICATIONS

This application is a division of co-pending U.S. patent application Ser. No. 14/198,900 filed Mar. 6, 2014, entitled RETRO GUIDEWIRE REAMER, which in turn claims benefit of the priority of U.S. Provisional Patent Application No. 61/776,896 filed Mar. 12, 2013, U.S. Provisional Patent Application No. 61/805,578 filed Mar. 27, 2013, and U.S. Provisional Patent Application No. 61/858,800 filed Jul. 26, 2013, the contents of which are incorporated by reference herein in their entirety for all purposes.

TECHNICAL FIELD

The present application relates generally to surgical apparatus and methods, and more specifically to surgical apparatus and methods of creating tunnels through bone tissue during arthroscopic ligament reconstruction surgery.

BACKGROUND

Desired outcomes for arthroscopic ligament reconstruction surgery are generally achieved by establishing the proper shape and placement of torn tissue. In a typical arthroscopic procedure, however, a cruciate footprint is often hidden from view by soft tissue, as well as remnant cruciate tissue. Such an arthroscopic procedure typically includes debriding the soft tissue and/or the remnant cruciate tissue to visualize the repair site, and establishing approach angles through portals located on the patient's skin. The reconstruction can then be accomplished by creating bone tunnels through the patient's femur and tibia. These bone tunnels are subsequently filled with a tendon graft, replicating the original damaged tissue.

The typical arthroscopic procedure described above has shortcomings, however, due at least in part to problems pertaining to the lack of visualization, the approach angles, and the shape of the tendon graft. Although the shape of the tendon graft is generally not round, that is often the shape of the reconstructed repair. Because the approach angles are generally not perpendicular to the skin surface, however, the portals located on the patient's skin are often visualized as being elliptical, making proper placement of the bone tunnels through the patient's femur and/or tibia difficult to achieve.

While performing arthroscopic ligament reconstruction surgery, a surgeon typically makes a small incision in a patient's skin covering the surgical site, e.g., a bone joint, to allow a surgical instrument(s) to be placed in the bone joint and manipulated through arthroscopic visualization. One such surgical instrument can be configured to operate in both a drilling mode and a cutting mode. The surgical instrument includes a shaft, and a drill bit portion having a conical, multi-blade configuration. The drill bit portion is configured to engage with the shaft, and to articulate between a "straight" position approximately parallel to the longitudinal axis of the shaft, and a "flip" non-parallel position relative to the longitudinal axis of the shaft. While operating in the drilling mode, the surgical instrument can be employed in an antegrade manner with the conical, multi-blade drill bit portion in the straight parallel position relative to the shaft's longitudinal axis. While operating in the cutting mode, the surgical instrument can be employed in a retrograde manner with the conical, multi-blade drill bit portion in the flip non-parallel position relative to the shafts longitudinal axis.

For torn knee anterior cruciate ligament (ACL) reconstruction, there has been an evolution in the anatomic femoral placement at the reconstructed ACL. One approach to achieving proper placement of the reconstructed ACL includes creating a tunnel from the outside to the inside (i.e., from the "outside in") of the patent's femur. With this approach, a guide can be used to establish a desired path for the femoral tunnel, and a guidewire can be placed along the desired path. A trans-tibial approach may then be employed, in which the knee is flexed to about 90°, the guide is placed in the center of the tibial footprint, and a tunnel is drilled through the tibia and extending into the femur. Alternatively, a flexible and/or retrograde drill may be employed, or the patient's knee may be hyper-flexed to allow the femoral and tibial tunnels to be drilled independent of one another.

Still another approach may be employed, in which the femoral/tibial tunnels are drilled through an anterior medial portal. With this approach, a curved guide can be used to place a guidewire, and an appropriately sized reamer can be advanced over the guidewire to create a bone tunnel. Alternatively, the patient's knee can be hyper-flexed to allow straight line drilling of the bone tunnel. A retro-drill can also be assembled inside the bone joint, and the bone tunnel can then be drilled in a retrograde manner.

SUMMARY

In accordance with the present application, surgical instruments and methods of using such surgical instruments (also referred to herein as a/the, "retro guidewire reamer(s)") are disclosed. In a first aspect, a retro guidewire reamer includes at least one cutting member, and a mechanism operative to move the cutting member, by remote activation, from a closed position to an opened or deployed position and vice versa, thereby allowing for the creation a counter bore through bone tissue (e.g., a tibia, a femur). In an exemplary mode of operation, a surgeon establishes a path through the bone for a guidewire using a guide, places the guidewire along the path, and removes the guide. The surgeon then establishes the proper size of a bone tunnel to best fit a replacement tendon graft. Once the proper size of the bone tunnel is established, the surgeon uses the retro guidewire reamer with an appropriately sized drill bit to create a primary bone tunnel over, the guidewire from the outside in. Once the primary bone tunnel is drilled, the surgeon retracts the guidewire, and activates the mechanism to open or deploy the cutting member within the bone joint to conform to the established size of the bone tunnel for the replacement tendon graft. The surgeon then uses the retro guidewire reamer with the opened or deployed cutting member to create a counter bore through the bone in a retrograde manner. Once the counter bore is drilled, the surgeon activates the mechanism to close the cutting member, allowing the retro guidewire reamer to be withdrawn through the primary bone tunnel created by the drill bit.

In a second aspect, a retro guidewire reamer includes a tubular shaft having a distal end, at least one cutting member disposed adjacent the distal end of the tubular shaft, and a first mechanism operative to move the cutting member from a closed position to an opened or deployed position. The tubular shaft is configured to be disposed over a guidewire, which can have at least one helix spline, flute, slot, thread, or any other suitable structural feature formed on a surface thereof. The cutting member includes at least one tab adapted to engage with the structural feature of the guidewire while the cutting member is disposed in the opened or deployed position, thereby securing the cutting member in the opened or deployed position. The retro guidewire reamer further includes a second mechanism operative to secure the guidewire within the tubular shaft while the cutting member is disposed in the opened or deployed position.

In a third aspect, a retro guidewire reamer includes a drill bit having a cannulated shaft with a longitudinal axis, and a cutting member configured as a small hollow segment with a central axis. The cutting member is pivotally, rotatably, or otherwise movably coupled at a distal end of the cannulated shaft such that it can pivot, rotate, or otherwise move between a first position where its central axis is coincident with the longitudinal axis of the shaft, and a second position where its central axis is disposed at an angle to the longitudinal axis of the shaft. The cutting member has a cannulated sidewall with sharpened edges at a forward circumferential end thereof, as well as sharpened edges on an outside surface thereof.

In a fourth aspect, a retro guidewire reamer includes a drill bit having a cannulated shaft with a longitudinal axis, and a cutting member configured as a small hollow segment with a central axis. The cutting member is pivotally, rotatably, or otherwise movably coupled adjacent a distal end of the cumulated shaft such that it can pivot, rotate, or otherwise move between a first position where its central axis is coincident with the longitudinal axis of the shaft, and a second position where its central axis is disposed at an angle to the longitudinal axis of the shaft. The cannulated shaft has sharpened edges at a forward circumferential end thereof, and the cutting member has a sidewall with sharpened edges on an outside surface thereof.

In a further exemplary mode of operation, a surgeon establishes a path through bone tissue for a guidewire using a guide, places the guidewire along the path, and then removes the guide. With the drill bit's cannulated shaft and cutting member in the first position (where its central axis is coincident with the longitudinal axis of the shaft) placed over the guidewire, the surgeon uses the retro guidewire reamer to drill a tunnel through the bone over the guidewire, from the outside in, in an antegrade manner. In accordance with the third aspect of the retro guidewire reamer described herein, the surgeon drills the bone tunnel using the sharpened edges at the forward circumferential end of the cutting member, in accordance with the fourth aspect of the retro guidewire reamer described herein, the surgeon drills the bone tunnel using the sharpened edges at the forward circumferential end of the cannulated shaft. Next, the surgeon retracts the guidewire to allow the cutting member to pivot, rotate, or otherwise move from the first position to the second position (where its central axis is disposed at an angle to the shaft's longitudinal axis). The surgeon then advances the guidewire and locks it to the cannulated shaft, for example, using a lock screw, thereby securing the cutting member in the angled second position. With the cannulated shaft paced over the guidewire and the cutting member in the second position, the surgeon drills a counter bore through the bone over the guidewire in a retrograde manner, using the sharpened edges on the outside surface of the cutting member's sidewall.

Using the disclosed retro guidewire reamers, a surgeon can advantageously deploy a cutting member within a bone joint with a single manual motion. Further, because the cutting member can be deployed within the bone joint by remote activation, the amount of bone joint space required for successful deployment of the cutting member is reduced. Moreover, by providing retro guidewire reamers that include a drill bit having a cannulated shaft, and a cutting member pivotally, rotatably, or otherwise movably coupled to the cannulated shaft and adapted to engage a guidewire at least while in an opened or deployed position, the retro guidewire reamers can be advantageously used with a guidewire for more accurate bone tunnel placement during arthroscopic ligament reconstruction surgery, such as ACL reconstruction surgery.

Other features, functions, and aspects of the invention will be evident from the Detailed Description that follows:

BRIEF DESCRIPTION OF THE DRAWINGS

The accompanying drawings, which are incorporated in and constitute a part of this specification, illustrate one or more embodiments described herein and, together with the Detailed Description, explain these embodiments. In the drawings:

FIGS. 1-5b illustrate an exemplary mode of operating exemplary retro guidewire reamer, in accordance with the present application;

FIGS. 6a and 6b illustrate the retro guidewire reamer employed in the mode of operation illustrated in FIGS. 1-5b;

FIGS. 10a-12b illustrate various as relating to the operation of the mechanism of FIGS. 9a and 9b;

FIGS. 17a-19b illustrate a first alternative embodiment of the retro guidewire reamer of FIGS. 6a and 6b;

FIGS. 22a-22c illustrate additional views of the retro guidewire reamer of FIGS. 20a and 20b, including an exemplary retro lock knob, an exemplary retro lock bushing ring, and an exemplary retro drive bushing;

FIGS. 23a-23m illustrate an exemplary mode of operating the retro guidewire reamer of FIGS. 20a and 20b;

DETAILED DESCRIPTION

The disclosures of U.S. Provisional Patent Application No. 61/776,896 filed Mar. 12, 2013 entitled RETRO GUIDEWIRE REAMER, U.S. Provisional Patent Application No. 61/806,578 filed Mar. 27, 2013 entitled RETRO GUIDEWIRE REAMER, and U.S. Provisional Patent Application No. 61/858,800 filed Jul. 26, 2013 entitled RETRO GUIDEWIRE LOCK REAMER, are hereby incorporated herein by reference in their entirety.

Figure 1:
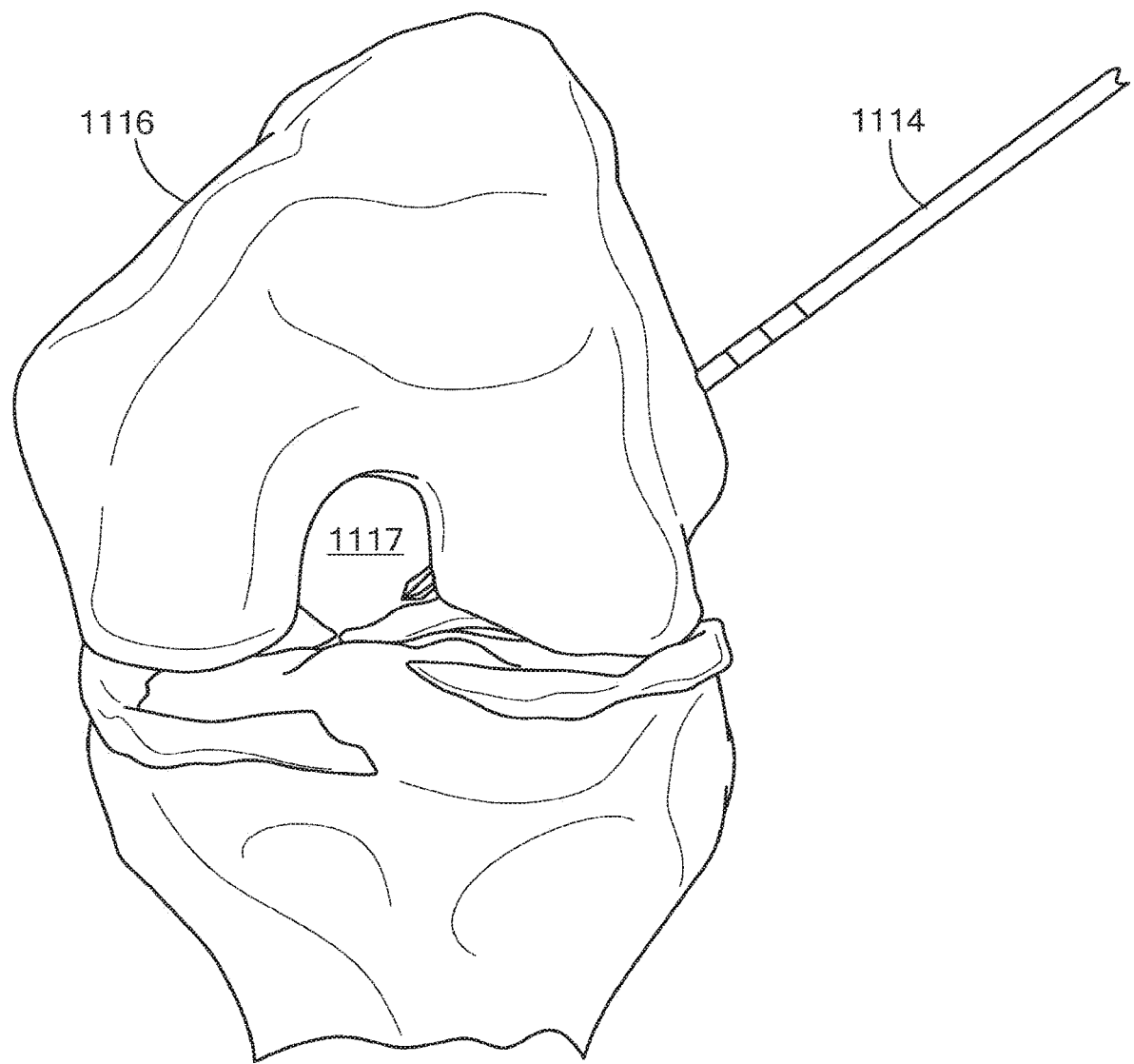
Figure 2A:
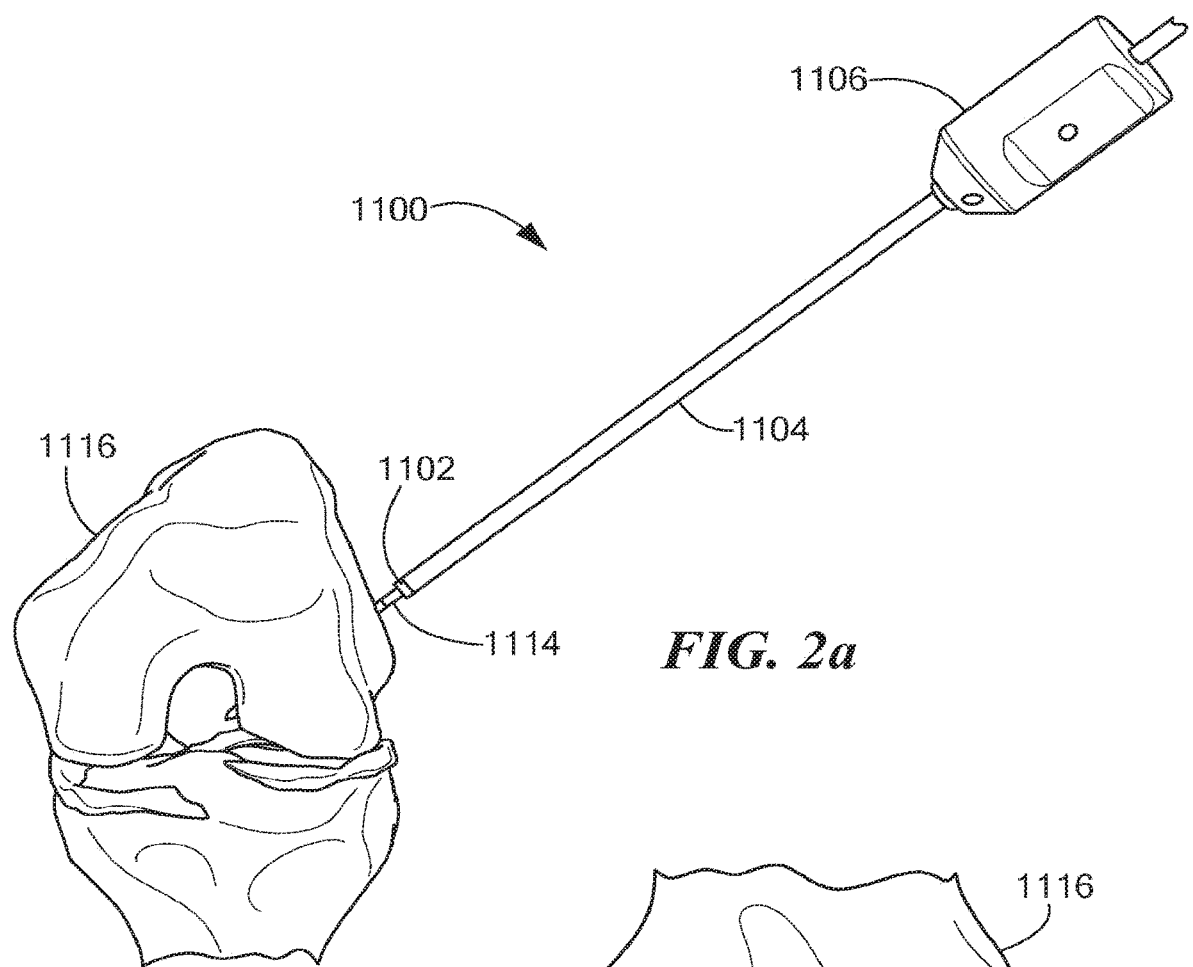
Figure 2B:
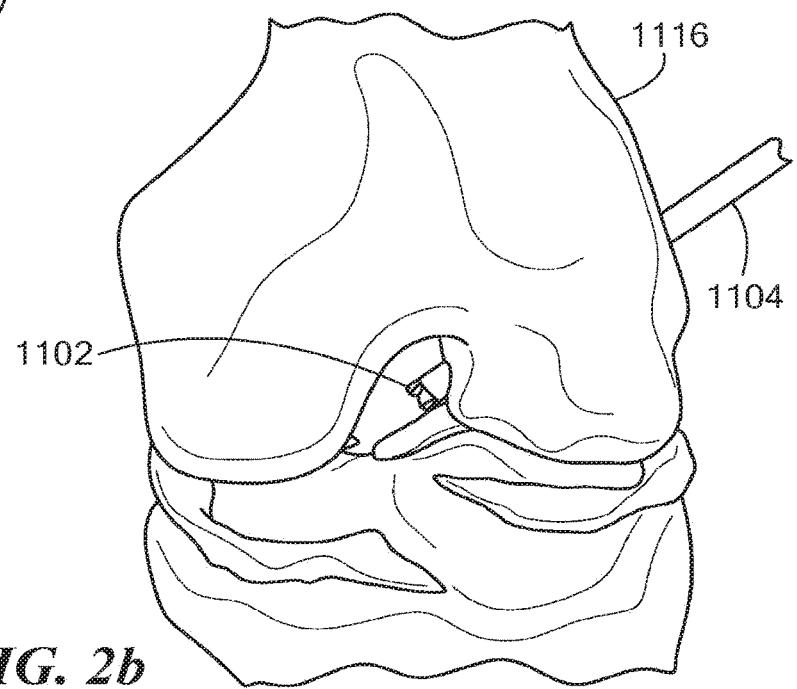
Figure 4:
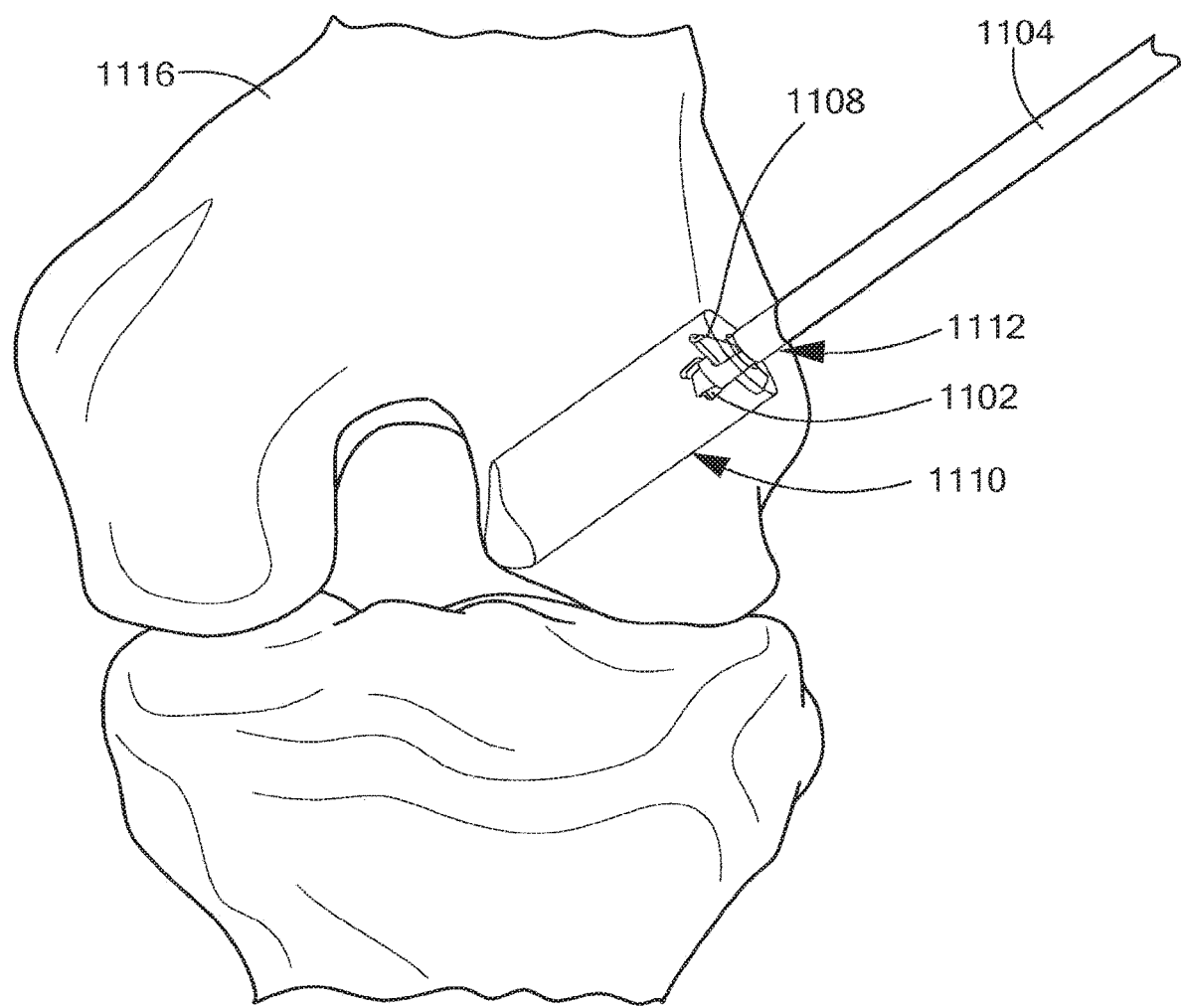
Figures 5A, 5B:
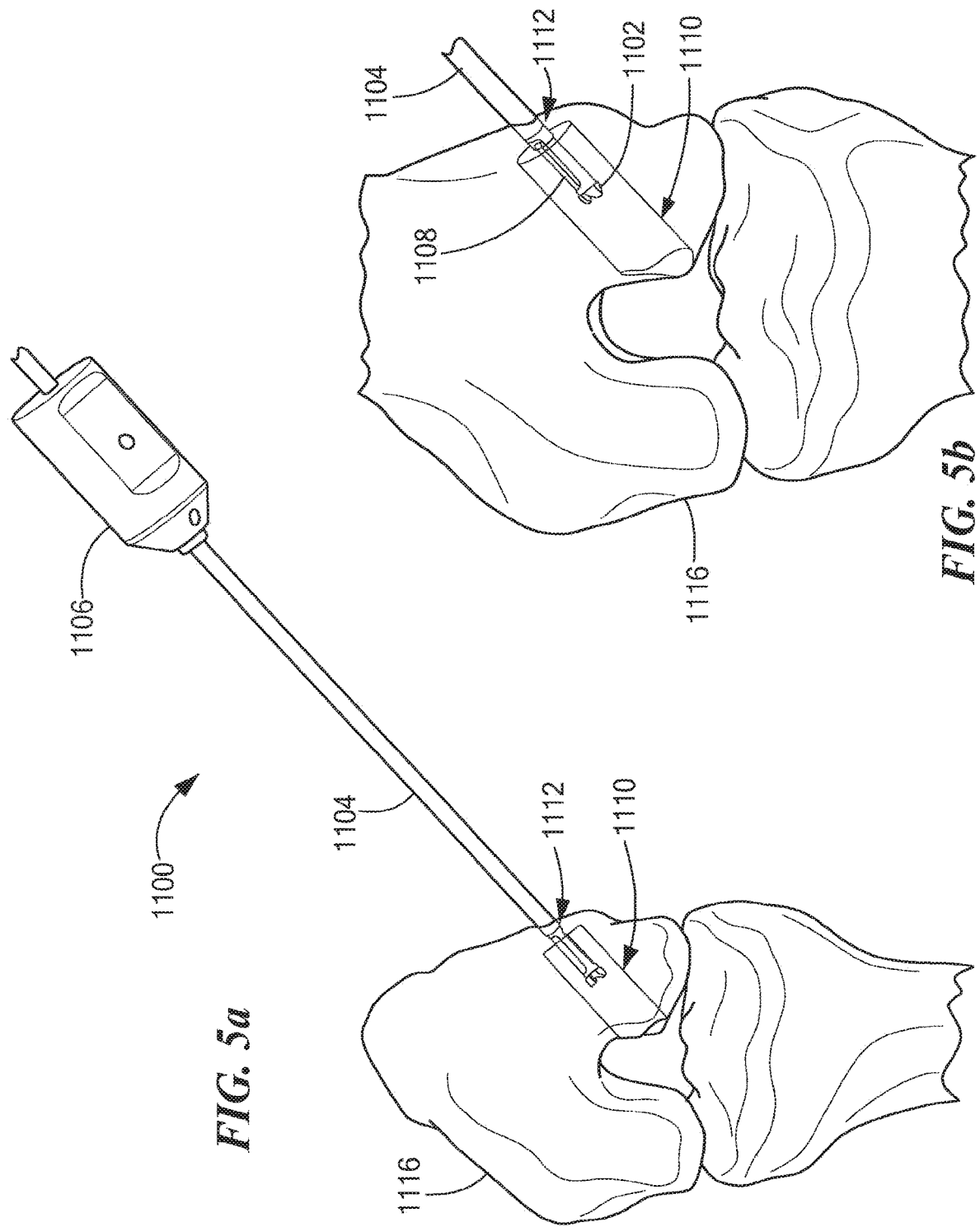

An exemplary mode of operating an illustrative embodiment of a retro guidewire reamer 1100 is described below with reference to FIGS. 1-5b, in accordance with the present application. As shown in FIG. 1, a surgeon establishes a desired path for a guidewire 1114 through femoral bone 1116. For example, the desired path may be established using a guide (not shown), such as a pinpoint guide or any other suitable guide. The surgeon places the guidewire 1114 along the desired path, and removes the guide. The surgeon can then determine the size of a primary bone tunnel 1112 (see FIG. 4), as well as the size of a counter bore 1110 (see FIG. 4) through the femoral bone 1116 appropriate to fit a replacement tendon graft, using any suitable technique known in the art. As shown in FIGS. 2a and 2b, using a drill bit 1102 appropriately sized to create the primary bone tunnel 1112 (e.g., the drill bit 1102 can be a 4.5 mm drill bit or any other suitable drill bit), the surgeon can use a power drill (not shown) to drill the primary bone tunnel 1112 through the femoral bone 1116 over the guidewire 1114 from the outside in. As shown in FIGS. 3a and 3b, the surgeon then at least partially retracts the guidewire 1114 and uses a mechanism 1106 to manually open deploy at least one cutting member 1108 (e.g., 1 or 2 such cutting members) within a bone joint 1117 (see also FIG. 1). In one embodiment, the surgeon can push or slide an outer tubular shaft 1104 toward the mechanism 1106 in the direction indicated by a directional arrow 1120 (see FIG. 3a), thereby causing the mechanism 1106 to open or deploy the cutting member 1108 within the bone joint 1117 in a single manual motion. As shown in FIG. 4, the surgeon then uses the power drill with the deployed cutting member 1108 to create the counter bore 1110 through the femoral bone 1116 in a retrograde manner. Once the counter bore 1110 is drilled, the surgeon activates the mechanism 1106 to close the cutting member 1108, allowing the retro guidewire reamer 1100 to be withdrawn through the primary bone tunnel 1112 created by the drill bit 1102 (see FIGS. 5a and 5b).

It is noted that, in the exemplary mode of operation described above, the counter bore 1110 may be drilled along the axis of the primary bone tunnel 1112, or at a predetermined angle to the primary bone tunnel axis. It is further noted that the retro guidewire reamer 1100 can be cannulated to allow fluid to pass through the tubular shaft during use, thereby clearing out any soft tissue that may potentially block the deployment of the cutting member 1108 within the bone joint 1117.

FIG. 6a depicts a side view of the retro guidewire reamer 1100, as well as a detailed view of the drill bit 1102 and the outer tubular shaft 1104 disposed over the guidewire 1114. FIG. 6b depicts a further side view of the retro guidewire reamer 1100, as well as a detailed view of the drill bit 1102, a tubular shaft 1103, and the cutting, member 1108 in its fully opened or deployed position. As shown in FIGS. 6a and 6b, the retro guidewire reamer 1100 includes the drill bit 1102 having the tubular (cannulated) shaft 1103, the cutting member 1108 operatively coupled near a distal end of the tubular shaft 1103, the elongated outer tubular shaft 1104, and the mechanism 1106 for manually opening or deploying the cutting member 1108. As discussed herein, the retro guidewire reamer 1100 can be advantageously used with the guidewire 1114 (e.g., a 2.4 mm guidewire, or any other suitable guidewire or guide pin) for more accurate bone tunnel placement during arthroscopic ligament reconstruction surgery, such as anterior cruciate ligament (ACL) reconstruction surgery.

Figure 7:
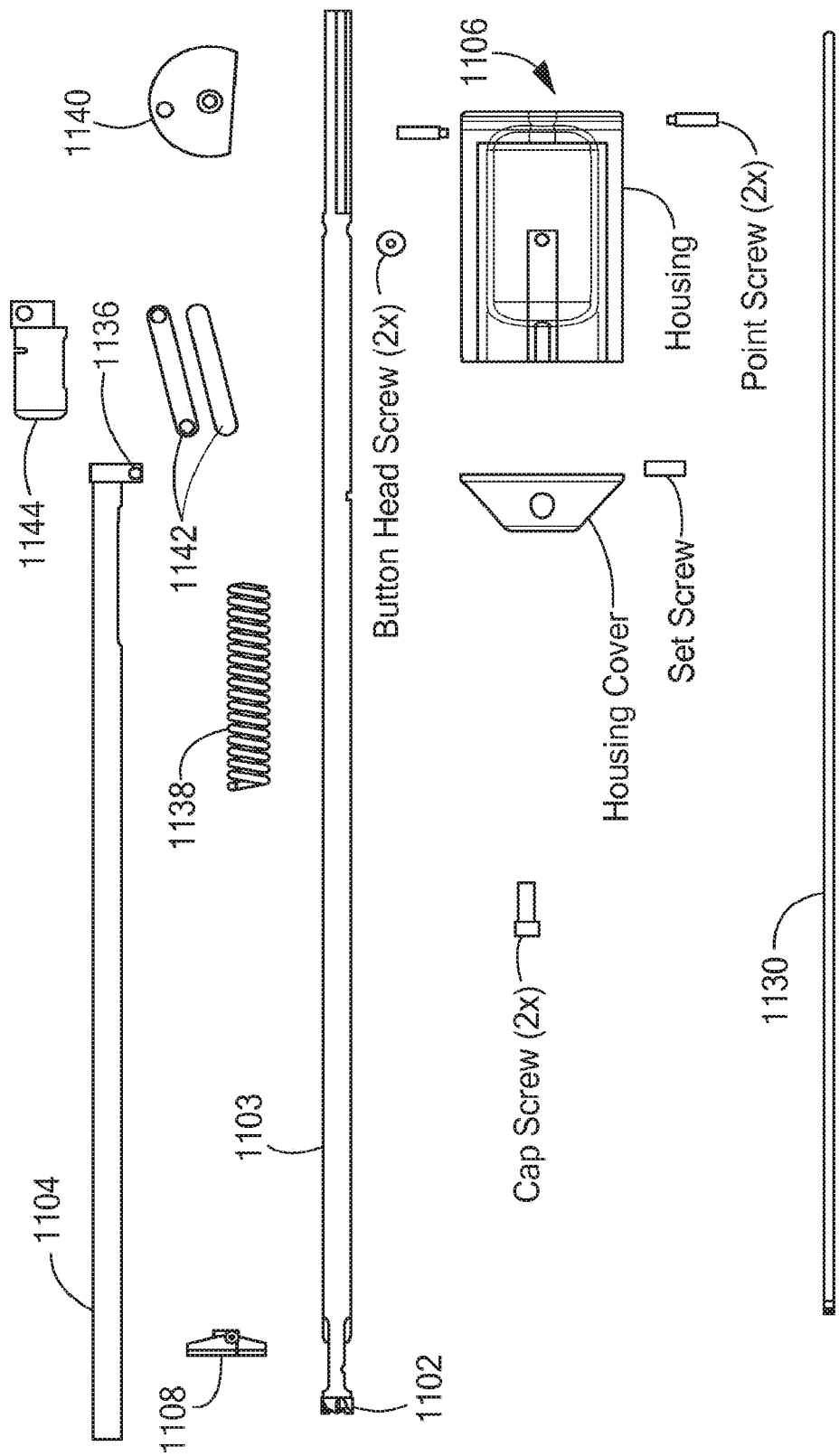
FIG. 7 illustrates various components included in the retro guidewire reamer of FIGS. 6a and 6b.

FIG. 7 depicts various components of the retro guidewire reamer 100, including the drill bit 1102, the tubular shaft 1103, the cutting member 1108, the outer tubular shaft 1104, and the mechanism 1106 for manually opening or deploying the cutting member 1108. FIG. 7 further depicts an actuator 1130, at least one tab 1136 located at a proximal end of the tubular shaft 1104, a compression spring 1138, a cam wheel 1140, at least one drive link 1142, and a bushing 1144, all of which are further described below.

Figure 8A:
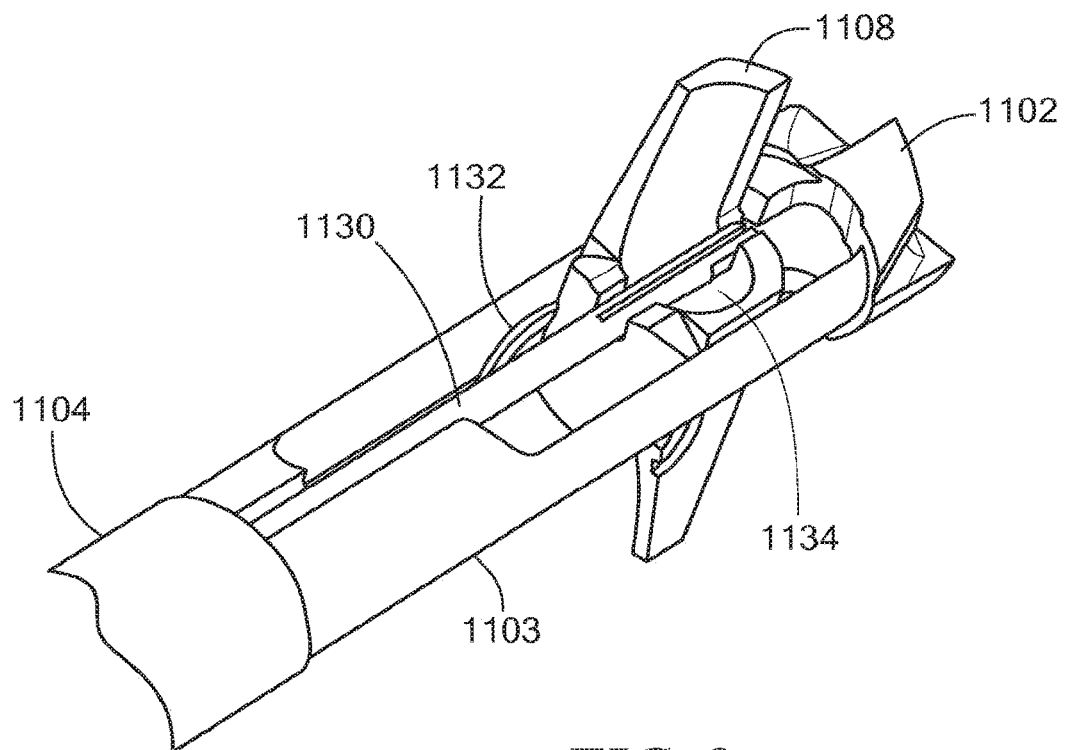
FIGS. 8a-8c illustrate an exemplary distal tip of the retro guidewire reamer of FIGS. 6a and 6b.
Figure 8B:
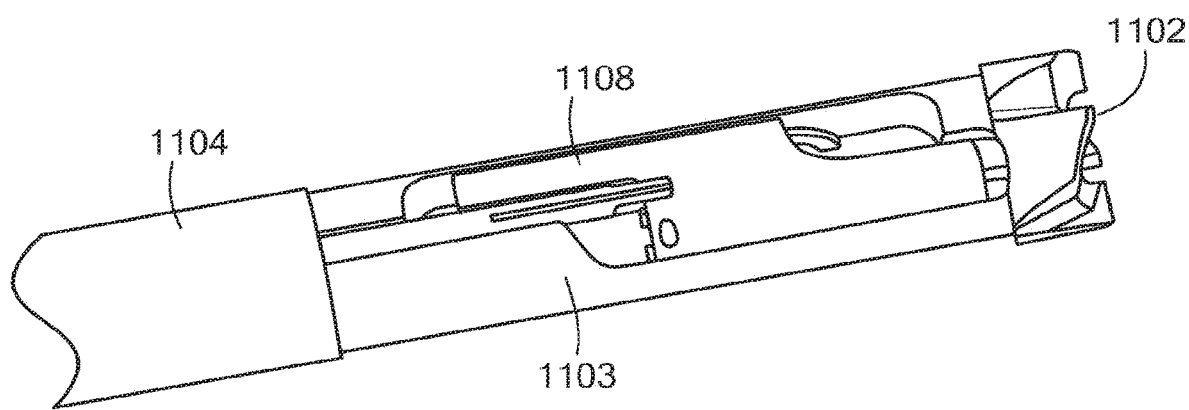

FIG. 8a depicts another detailed view of the drill bit 1102, the tubular shaft 1103, the outer tubular shaft 1104, and the cutting member 1108 in its fully opened or deployed position. FIG. 8a further depicts the actuator 1130 and a lug configuration 1132 for use in conjunction with the mechanism 1106 for opening or deploying the cutting member 1108. The actuator 1130 and the lug configuration 1132 are also further described below. In addition, FIG. 8a depicts a hole 1134 through the cutting member 1108 that is adapted to accommodate the guidewire 1114 while the cutting member 1108 is in its closed position. FIG. 8b depicts a detailed view of the cutting member 1108 in its closed position.

Figure 8C:
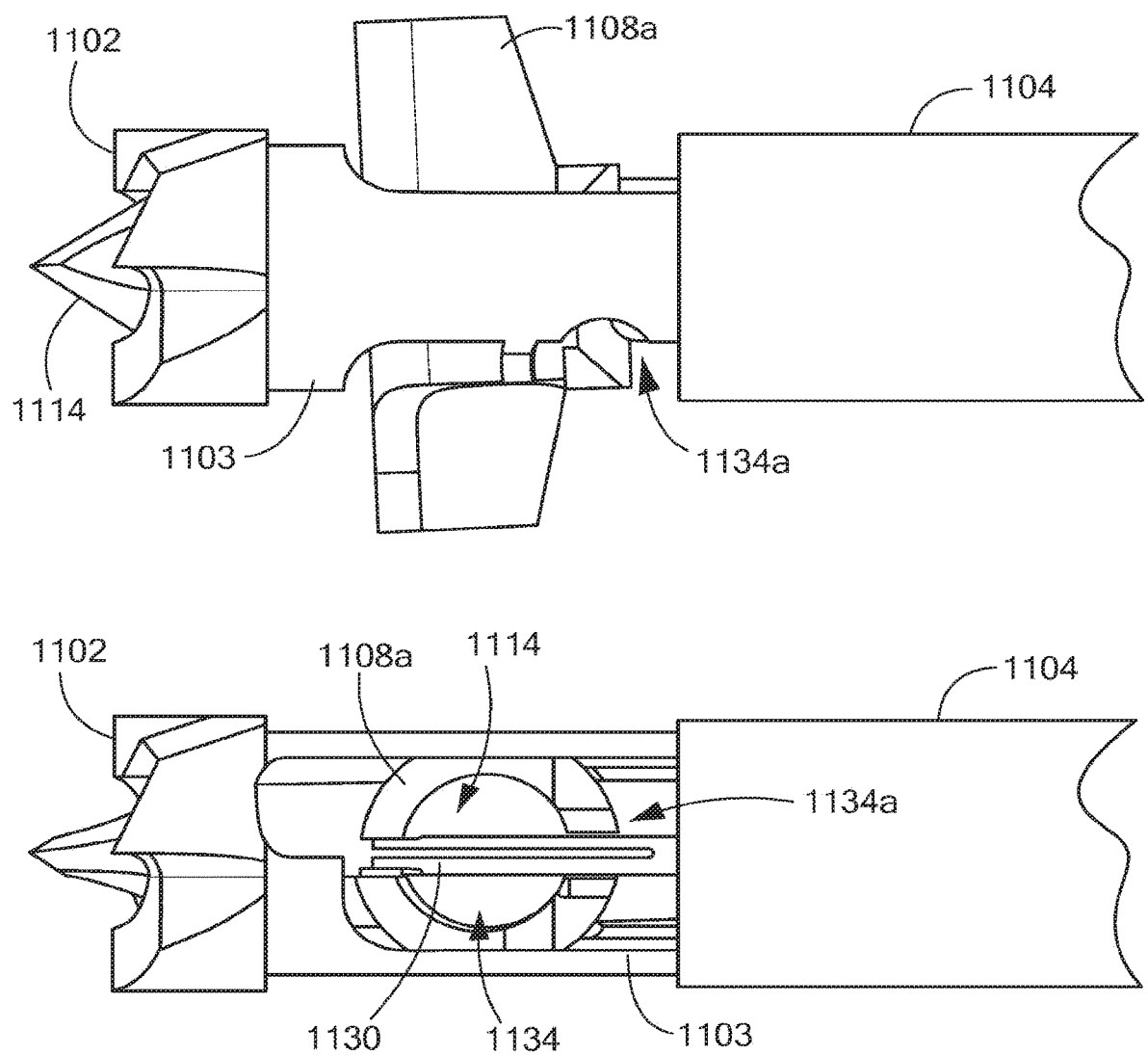

FIG. 8c depicts a further detailed view of the drill bit 1102, the tubular shaft 1103, and the outer tubular shaft 1104, as well as an alternative embodiment 1108a of the cutting member in its fully deployed position. FIG. 8c further depicts a hole 1134a (see also FIG. 13c) through the cutting member 1108a that is adapted to accommodate the guidewire 1114, thereby securing the cutting member 1108a in its deployed position.

Figure 9A:
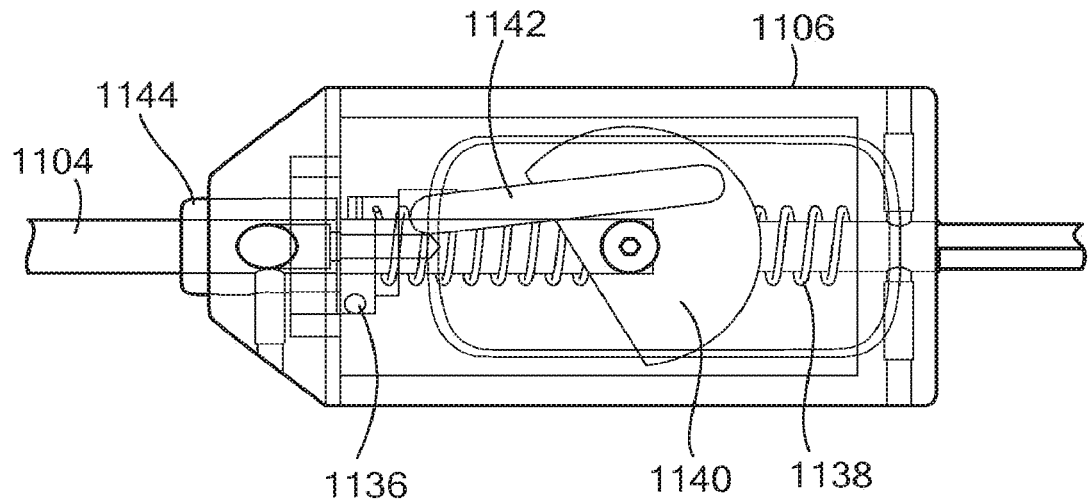
FIGS. 9a and 9b illustrate an exemplary mechanism or deploying a cutting member included in the retro guidewire reamer of FIGS. 6a and 6b.
Figure 9B:
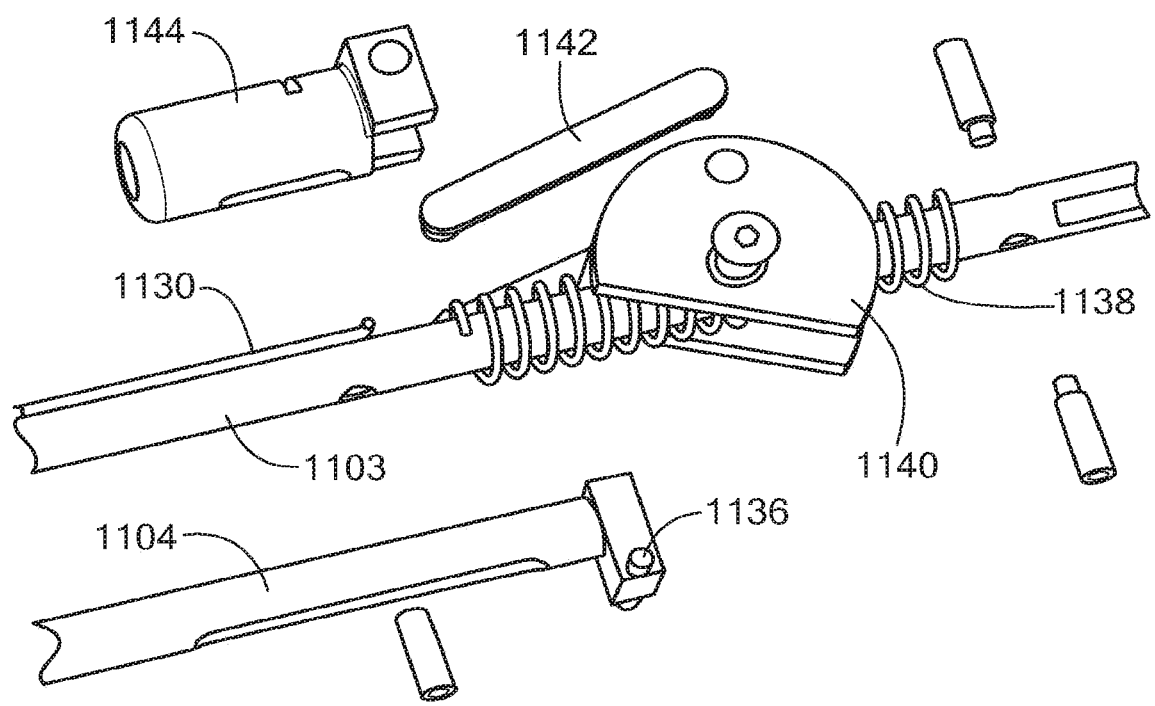

FIG. 9a depicts a detailed view of the outer tubular shaft 1104 and the mechanism 1106, as well as a detailed view of various components within a mechanism housing 1156 (see also FIG. 15), including the tab 1136 located at the proximal end of the tubular shaft 1104, the compression spring 1138, the cam wheel 1140, and the drive link 1142 interconnecting the cam wheel 1140 and the bushing 1144. FIG. 9b depicts an exploded view of the various components within the mechanism housing 1156, further including the actuator 1130 connectable between the cutting member 1108 and the bushing 1144.

As described above with reference to FIGS. 3a and 3b, a surgeon can push or slide the outer tubular shaft 1104 toward the mechanism 1106 in the direction indicated by the directional arrow 1120 to cause the mechanism 1106 to open or deploy the cutting member 1108 in a single manual motion. As shown in FIGS. 10a and 10b, as the outer tubular shaft 1104 is pushed toward the mechanism 1106, the tab 1136 comes in contact with the cam wheel 1140, causing the cam wheel 1140 to rotate in the counter clockwise (CCW) direction and compressing the compression spring 1138 (see FIG. 10b). As shown in FIGS. 10b and 11a, as the cam wheel 1140 rotates in the CCW direction and the compression spring 1138 becomes increasingly compressed, the drive link 1142 moves the bushing 1144 toward the distal end of the tubular shaft 1103, thereby causing the actuator 1130 to open or deploy the cutting member 1108.

Once the compression spring 1138 is fully compressed and the cutting member 1108 is fully deployed (see FIG. 11*a*), the surgeon can gradually release the outer tubular shaft 1104 to allow the compression spring 1138 to push the tubular shaft 1104 against the cutting member 1108 (see FIG. 11*b*), preventing the cutting member 1108 from moving from its deployed position.

As shown in FIGS. 12*a* and 12*b*, to move the cutting member 1108 from its opened or deployed position back to its closed position, the surgeon can again push or slide the outer tubular shaft 1104 in the direction indicated by a directional arrow 1122 (see FIG. 12*b*) to partially compress the compression spring 1138 as well as partially expose the tubular shaft 1103, and then push the bushing 1144 toward the mechanism 1106 to rotate the cam wheel 1140 in the clockwise (CW) direction (see FIG. 12*b*), thereby causing the actuator 1130 to move the cutting member 1108 to its closed position.

Figure 13C:
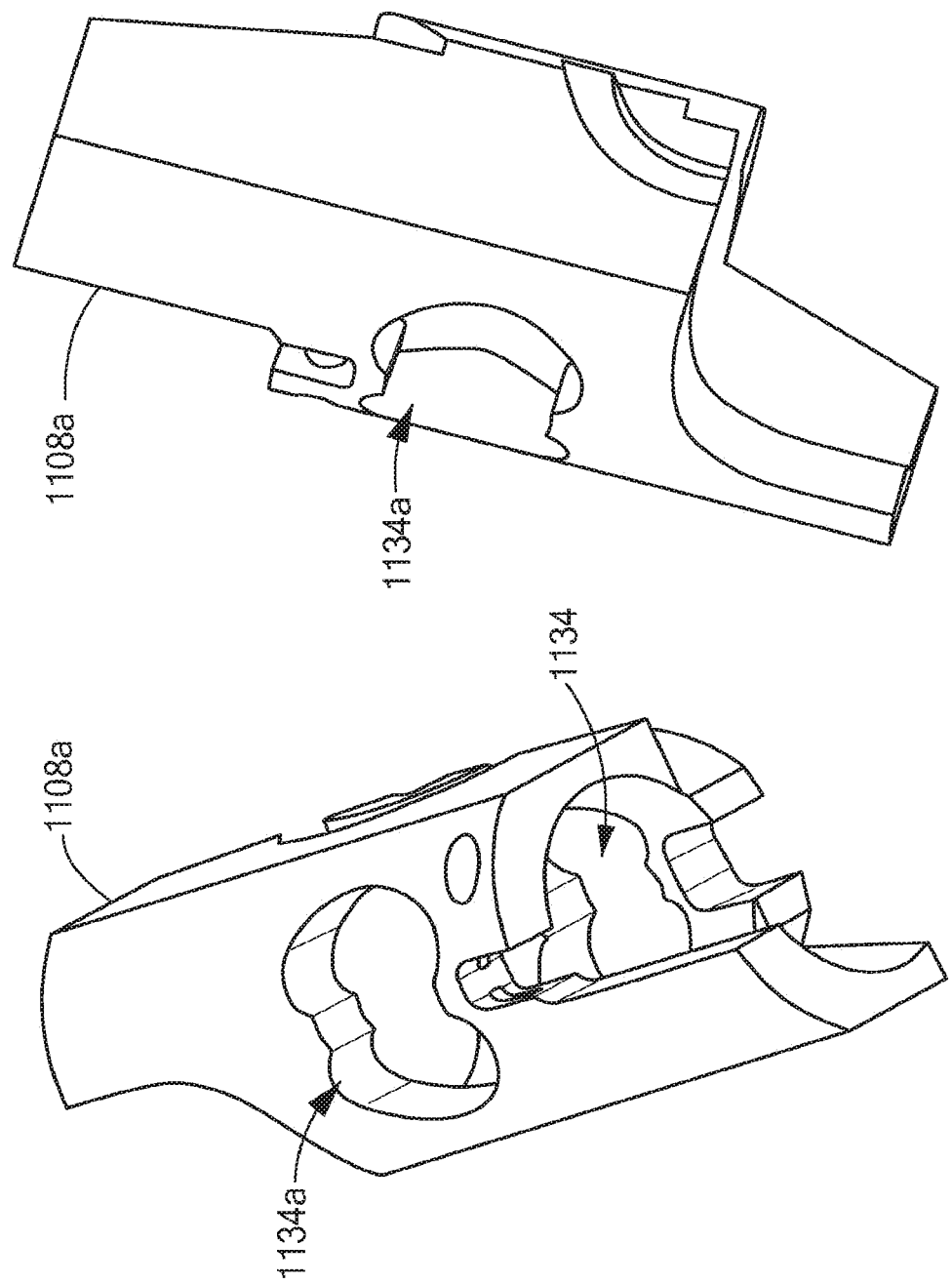
FIGS. 13a-16 illustrate various aspects relating to the operation and assembly of the retro guidewire reamer of FIGS. 6a and 6b.

FIGS. 13*a*-16 illustrate various exemplary aspects relating to the operation and assembly of the disclosed retro guidewire reamer 1100. As shown in FIG. 13*a*, the lug configuration 1132 (see also FIG. 8*a*) includes one or more internal lugs 1132.1 on the cutting member 1108 that are configured to slide over corresponding external lugs 1132.2 on the tubular shaft 1103. As shown in FIG. 13*b*, the actuator 1130 is configured to snap into a side hole 1146 formed in the cutting member 1108. FIG. 13*c* depicts the alternative embodiment 1108*a* of the cutting member 1108, including the holes 1134 and 1134*a* adapted to accommodate the guidewire 1114 while the cutting member 1108*a* is in its closed and opened or deployed positions, respectively.

Figure 14A:
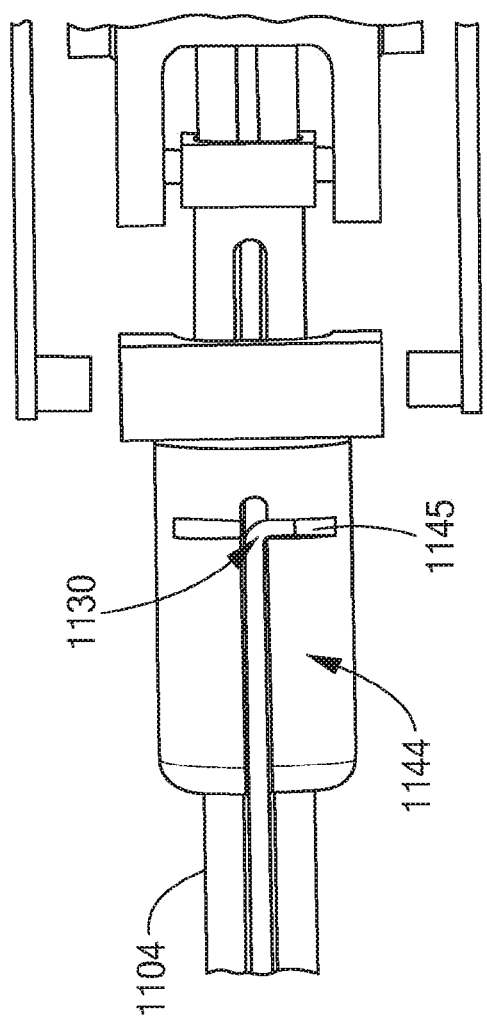
Figure 14B:
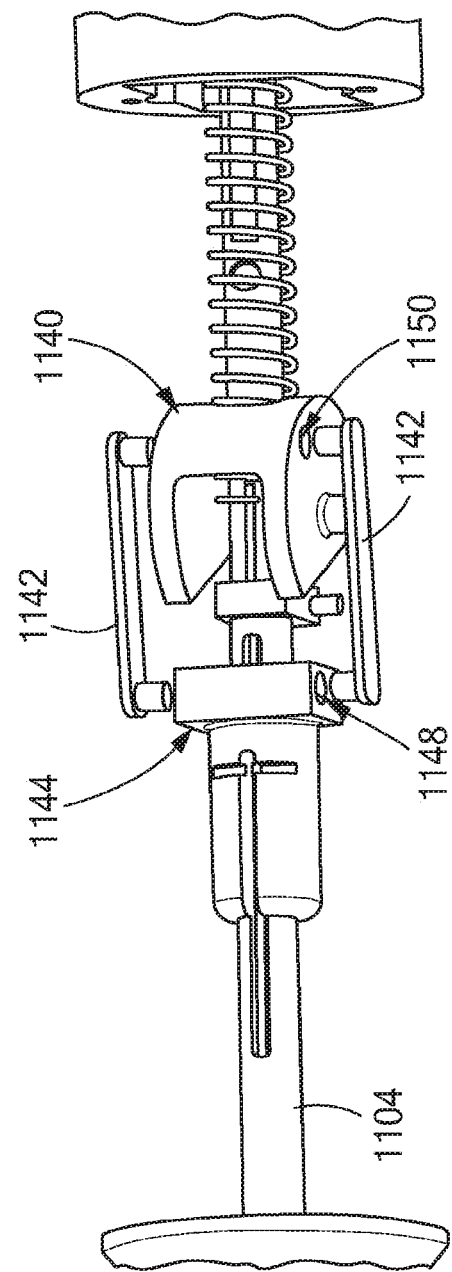
Figure 15:
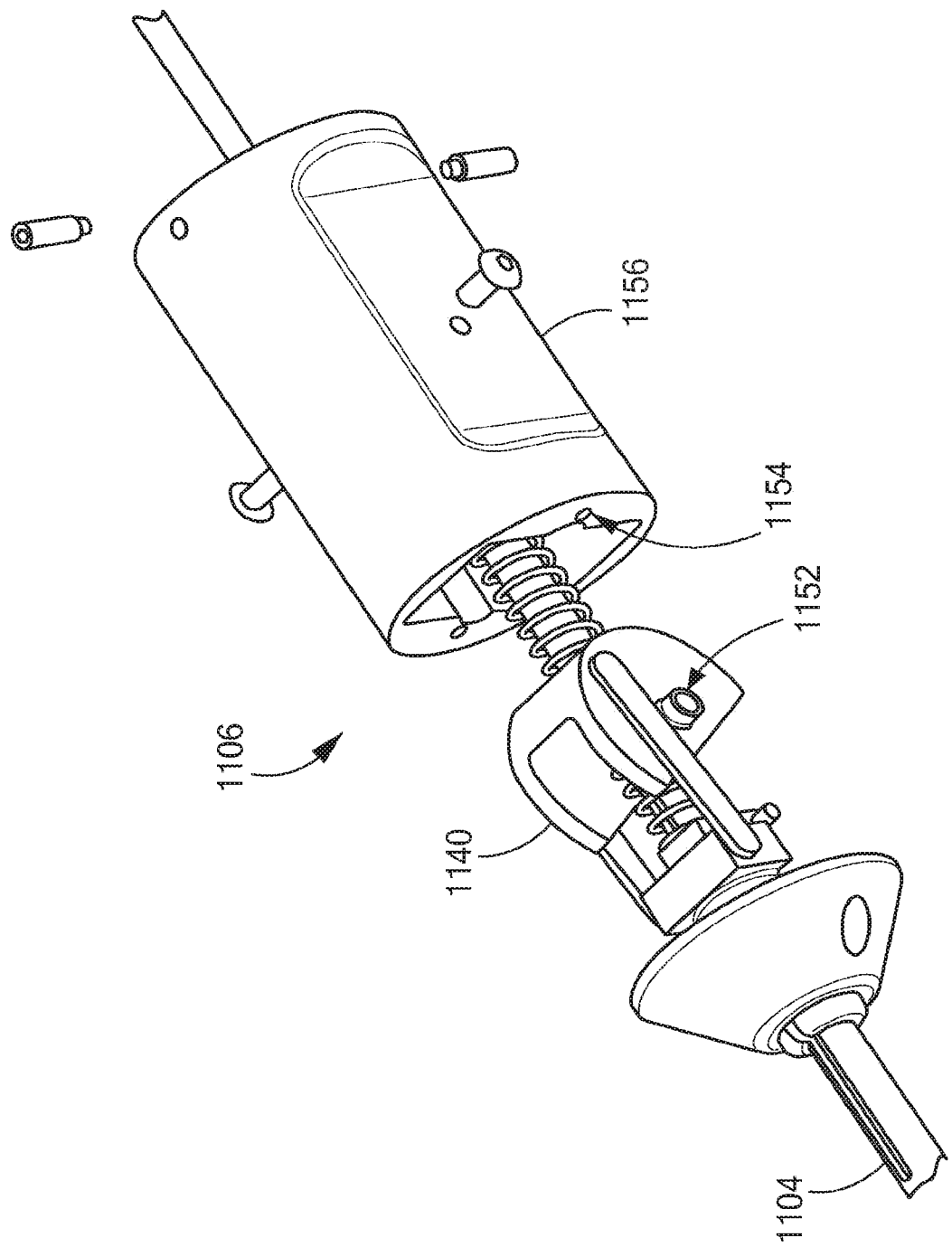
Figure 16:
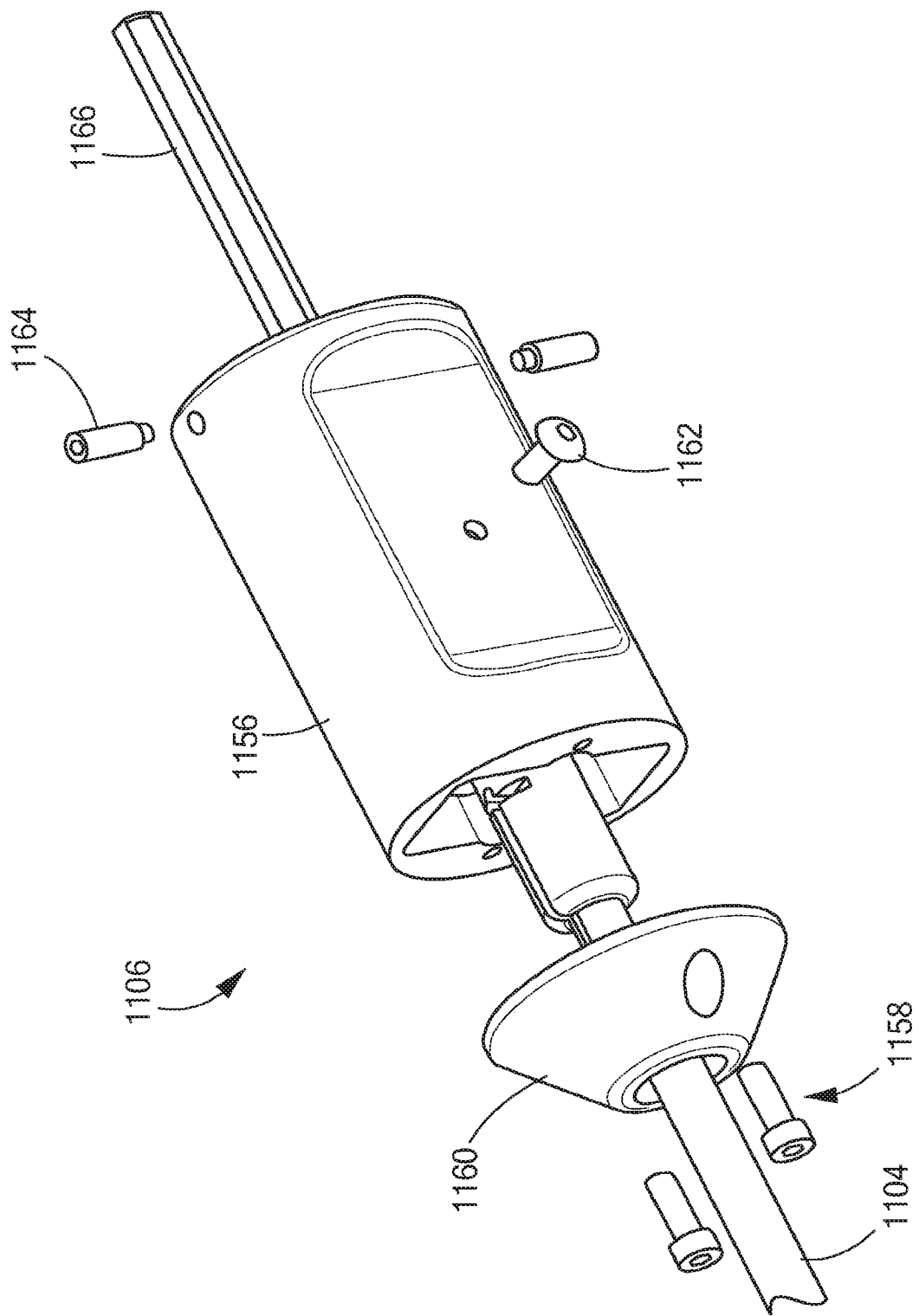
Figure 18:
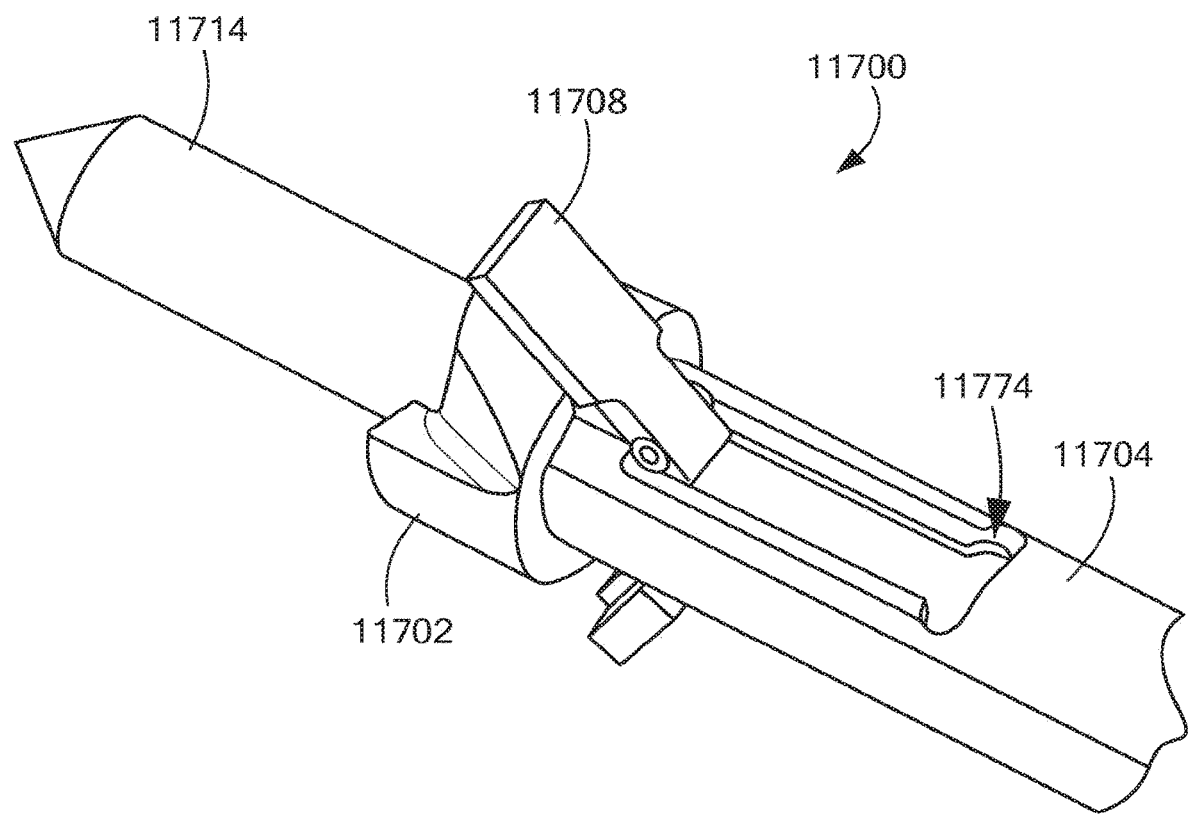

As shown in FIG. 14*a*, the actuator 1130 is configured to slide into a slot hole 1145 formed in the bushing 1144. As shown in FIG. 14*b*, the drive links 1142 are configured slide into holes 1148, 1150 formed it the bushing 1144 and the cam wheel 1140, respectively. As shown in FIG. 15, at least one hub 1152 on the cam wheel 1140 is configured to slide into at least one corresponding groove slot 1154 formed in the mechanism housing 1156. As shown in FIG. 16, at least one cap screw 1158 can be employed to secure a housing cover 1160 to the mechanism housing 1156. Further, at least one button head screw 1162 can be employed to secure the cam wheel 1140, as well as the various components attached to the cam wheel 1140, within the mechanism housing 1156. In addition, at least one set screw 1164 can be employed to secure the mechanism housing 1156 to a portion of a drill 1166.

FIGS. 17*a*-19*b* depict various exemplary aspects relating to an alternative embodiment 11700 of the retro guidewire reamer 1100. As shown in FIG. 17*a*, the retro guidewire reamer 11700 includes a drill bit 11702, an elongated outer tubular shaft 11704, and one or more cutting members 11708 (e.g., 1 or 2 cutting members). Like the retro guidewire reamer 1100, the retro guidewire reamer 11700 can be advantageously used with a guidewire 11714 (e.g., a 2.4 mm guidewire, or any other suitable guidewire or guide pin) for more accurate bone tunnel placement during arthroscopic ligament reconstruction surgery, such as ACL reconstruction surgery.

Figure 19A:
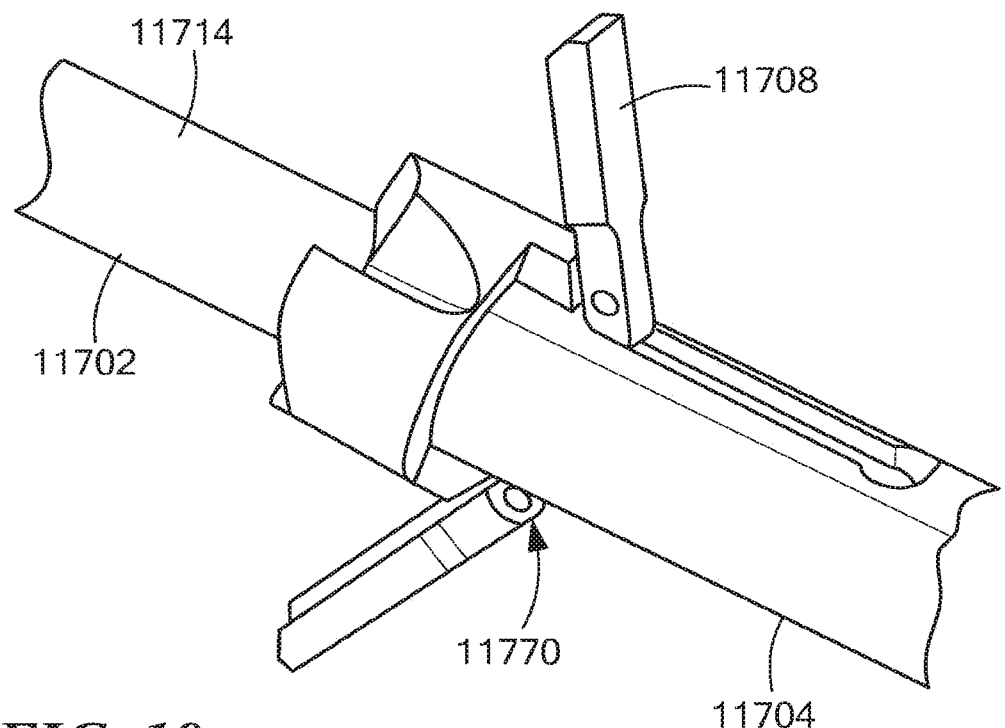
Figure 19B:
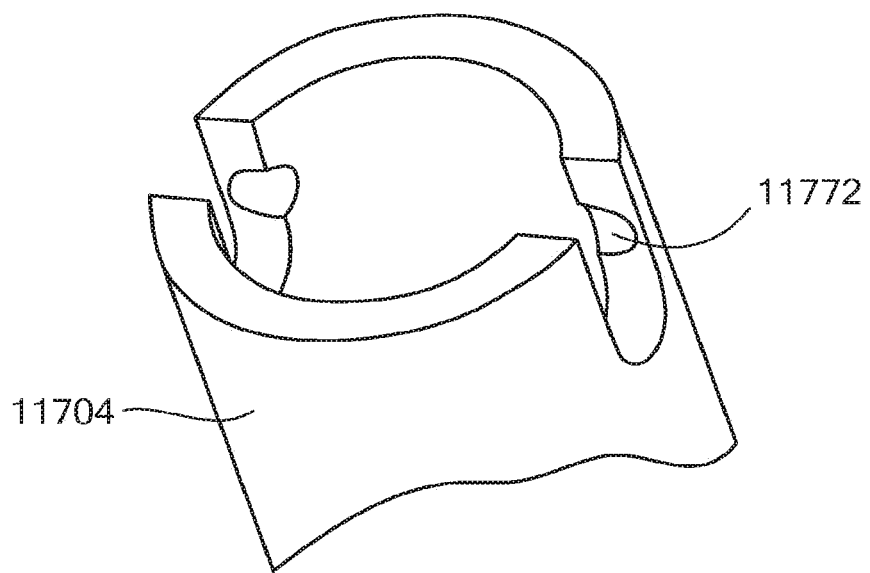

As shown in FIGS. 19*a* and 19*b*, the cutting members 11708 are attached to the outer tubular shaft 11704 by a ball and socket connection 11770, 11772. The cutting members 11708 are configured to move axially with the outer tubular shaft 11704, and to rotate via the ball and socket connection 11770, 11772. The ball and socket connection 11770, 11772 is integrated into the cutting members 11708 and the outer tubular shaft 11704, respectively, advantageously providing a "pin-less" design. Each "male" ball (see reference numeral 11770) is integrated into one of the cutting members 11708, and each "female" socket (see reference numeral 11772) is integrated into the outer tubular shaft 11704. Further embodiments of the retro guidewire reamer 11700 may employ at least one pin (not shown) to connect the cutting members 11708 to the outer tubular shaft 11704.

During an arthroscopic procedure, a surgeon can push or slide the outer tubular shaft 11704 toward the drill bit 11702 to cause the cutting members 11708 to impinge against a stop on the drill bit 11702 and to rotate outward, thereby opening or deploying the cutting members 11708 in a single manual motion. The outer tubular shaft 11704 disposed against the drill bit 11702 prevents the cutting members 11708 from moving from their opened or deployed positions (FIGS. 17*b* and 17*d*). The surgeon can subsequently push the outer tubular shaft 11704 away from the drill bit 11702 to cause the cutting members 11708 to rotate inward back to their closed positions (see FIGS. 17*a* and 17*c*).

To facilitate assembly of the retro guidewire reamer 1700, an assembly slot 11774 (see FIG. 18) can be provided to allow the cutting members 11708 to be fully inserted into the inner diameter of the retro guidewire reamer 11700, and to allow the outer tubular shaft 11704 to be advanced to the proper location for alignment of the ball and socket connection 11770, 11772. Once the female socket 11772 is aligned with the assembly slot 11774, the cutting members 11708 can be rotated outward until the male ball 11770 resides within the female socket 11772. At that point, the outer tubular shaft 11704 with the cutting members 11708 attached thereto can be advanced distally beyond the assembly slot 11774.

Figure 20A:
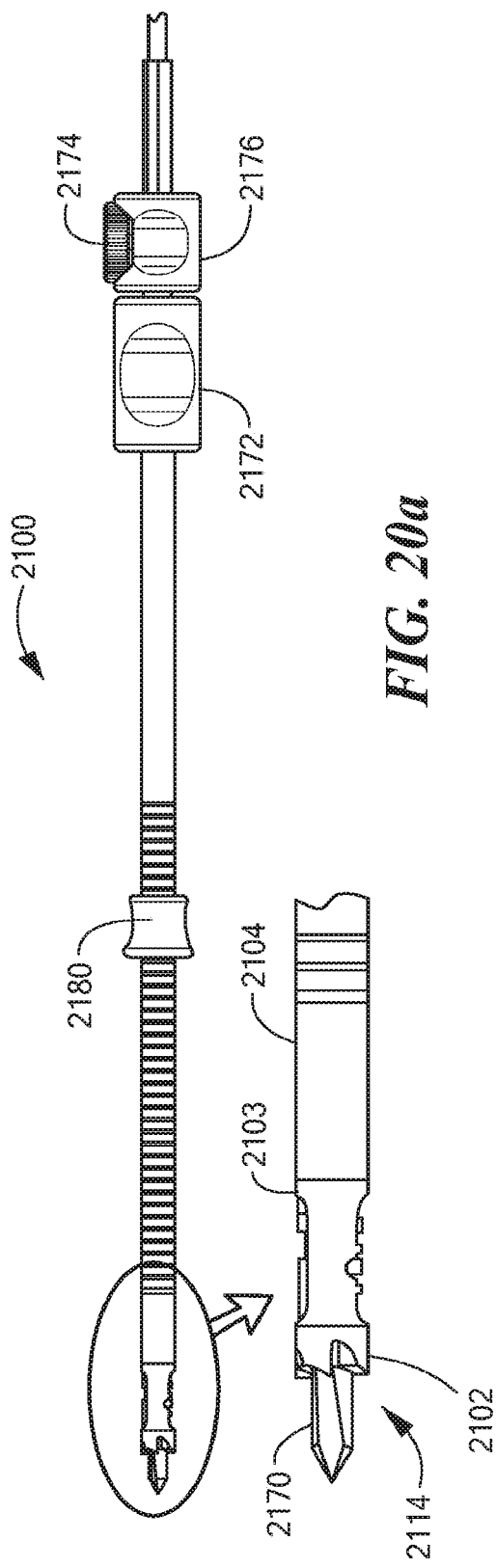
FIGS. 20a and 20b illustrate a second alternative embodiment of the retro guidewire reamer of FIGS. 6a and 6b.
Figure 20B:
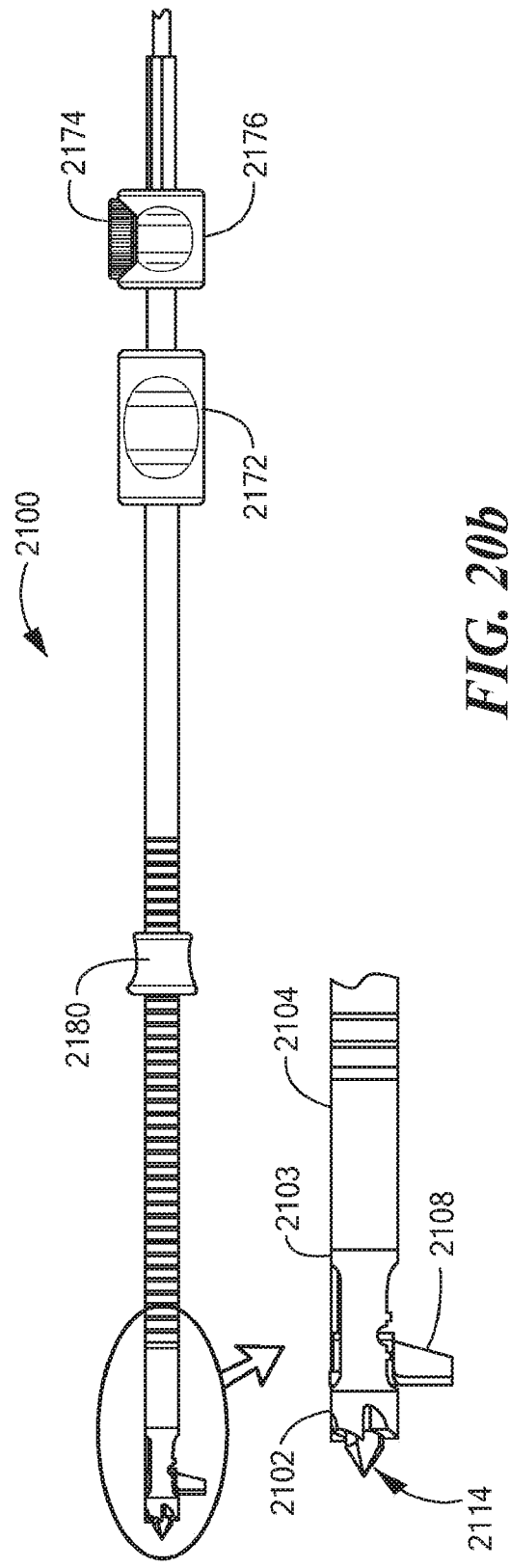

FIGS. 20*a* and 20*b* depict a further illustrative embodiment of an exemplary retro guidewire reamer 2100, in accordance with the present application. As shown in FIGS. 20*a* and 20*b*, the retro guidewire reamer 2100 includes a drill bit 2102 having a tubular (cannulated) shaft 2103, at least one cutting member 2108 operatively coupled near a distal end of the tubular shaft 2103, an elongated outer tubular shaft 2104, a retro drive bushing 2172, a retro lock knob 2174, a retro lock bushing ring 2176, and a depth slide 2180. FIG. 20*a* further depicts a detailed view of the drill bit 2102, the tubular shaft 2103, and the outer tubular shaft 2104 disposed over a guidewire 2114. FIG. 20*b* further depicts a detailed view of the drill bit 2102, the tubular shaft 2103, the outer tubular shaft 2104, and the cutting member 2108 in its fully opened or deployed position. The retro guidewire reamer 2100 can be advantageously used with the guidewire 2114 (e.g., a 2.4 mm guidewire, or any other suitable guidewire or guide pin) for more accurate bone tunnel placement during arthroscopic ligament reconstruction surgery, such as AOL reconstruction surgery.

Figure 21A:
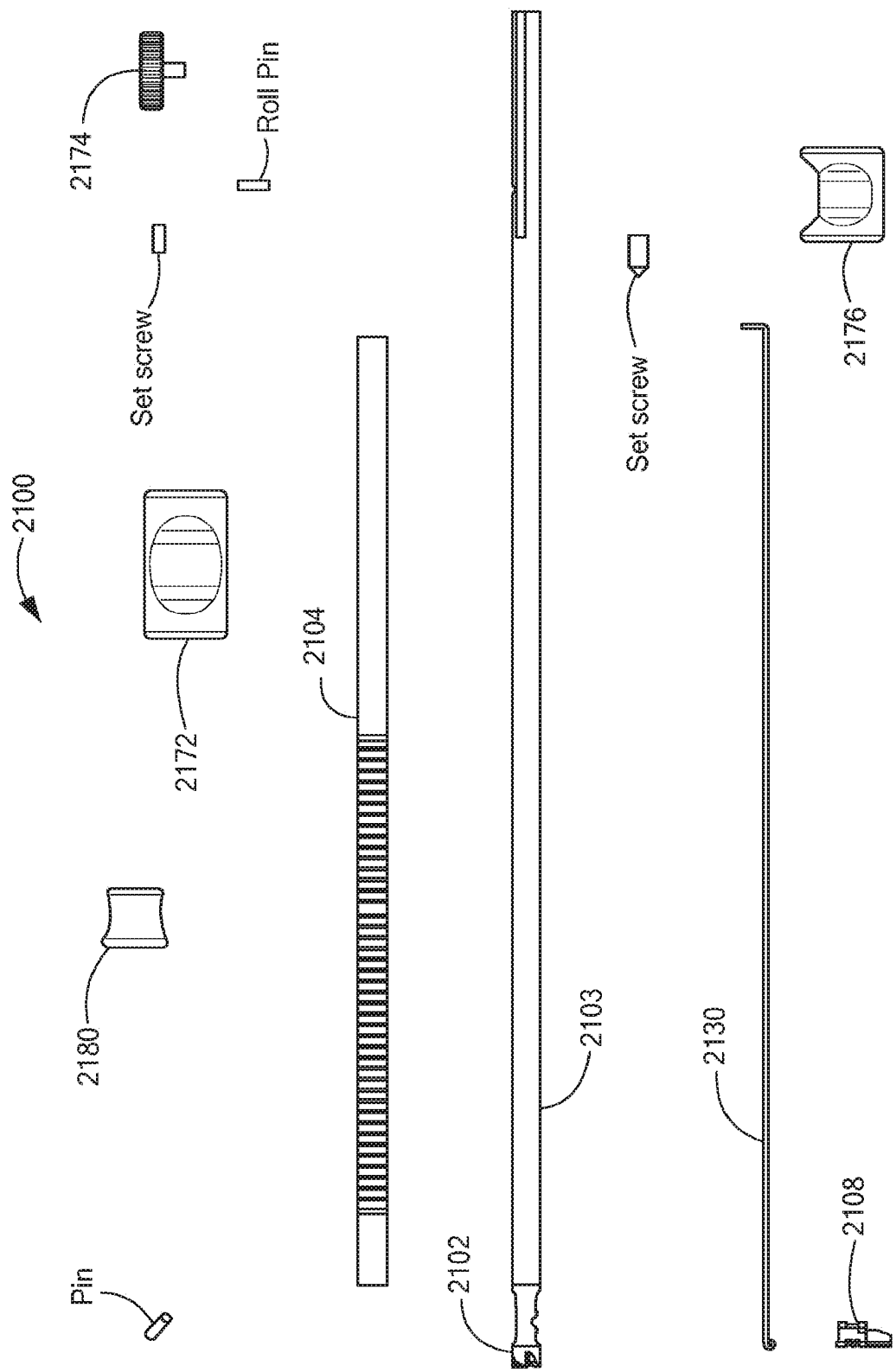
FIGS. 21a and 21b illustrate various components included in the retro guidewire reamer of FIGS. 20a and 20b.
Figure 21B:
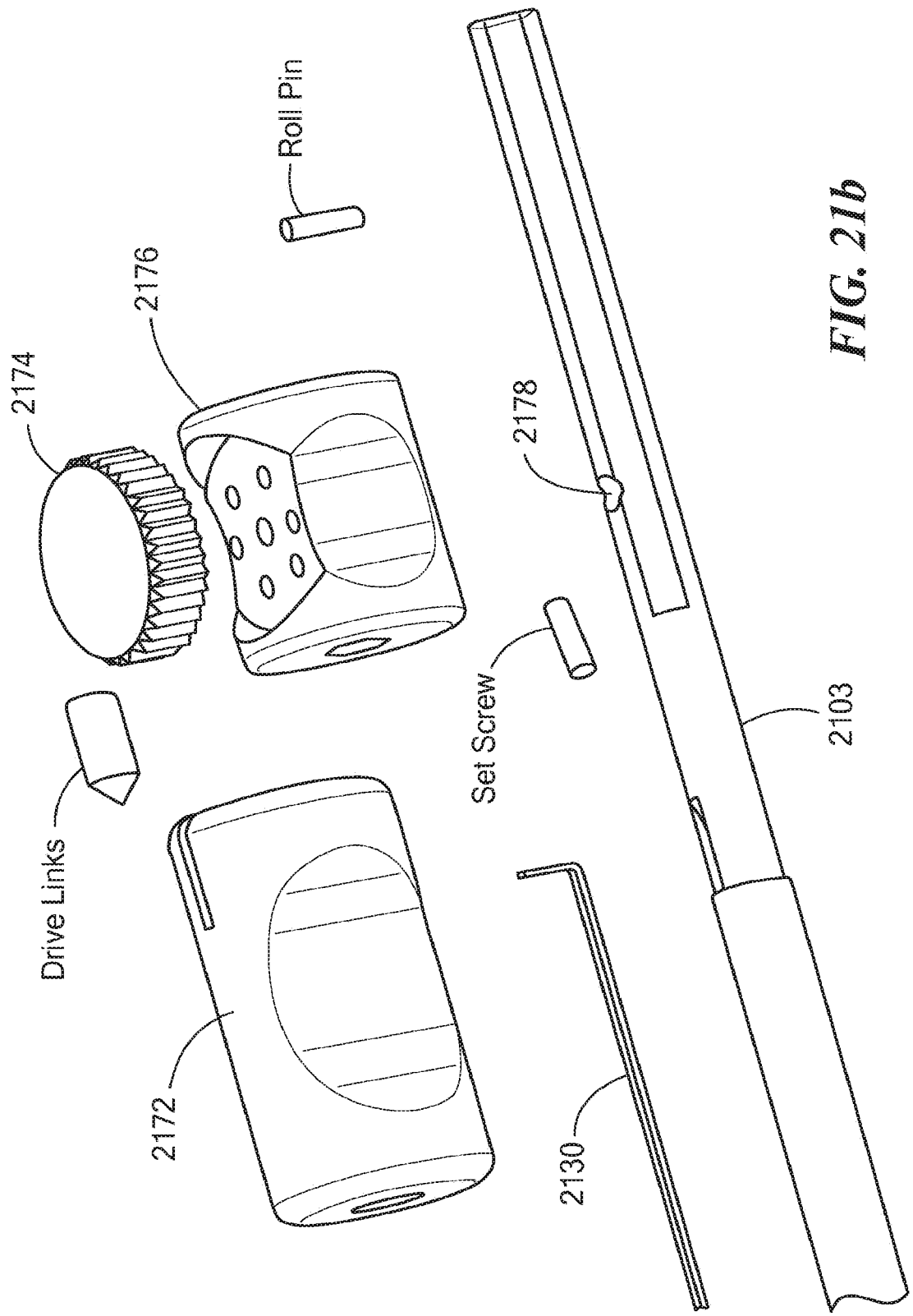

FIGS. 21*a* and 21*b* depict various components of the disclosed retro guidewire reamer 2100, including the drill bit 2102, the tubular shaft 2103, the cutting member'2108, the outer tubular shaft 2104, the retro drive bushing 2172, the depth slide 2180, a retrograde actuator 2130, the retro lock knob 2174, and the retro lock bushing ring 2176. The retro lock knob 2174 can have a pin or projection configured to engage a hole 2178 (see FIG. 21*b*) in the tubular shaft 2103, and to make contact with the guidewire 2114 disposed in the tubular shaft 2103. During use, the retro drive bushing 2172 and the retrograde actuator 2130 cooperate to move the cutting member 2108 from a closed position to its opened or deployed position, and vice versa. Further, during use, the retro lock knob 2174 and the retro lock bushing ring 2176 cooperate to secure the guidewire 2114 within the tubular shaft 2103, and to stabilize and strengthen the guidewire 2114 the tubular shaft 2103, and the cutting member 2108 as a unit, as further described herein.

FIGS. 22a-22c depict additional views of the retro guidewire reamer 2100 of FIGS. 20a and 20b, including the drill bit 2102, the tubular shaft 2103, the cutting member 2108, the outer tubular shaft 2104, the retro lock knob 2174, the retro lock bushing ring 2176, and the retro drive bushing 2172. As shown in FIG. 22a, the tubular shaft 2103 is configured to be disposed over the guidewire 2114. As shown in FIG. 22b, once the guidewire 2114 is at least partially retracted within the tubular shaft 2103, the retro drive bushing 2172 can be moved along the cuter tubular shaft 2104 toward the distal end of the tubular shaft 2103, causing the retrograde actuator 2130 to move the cutting member 2108 to its deployed position.

Figure 22D:
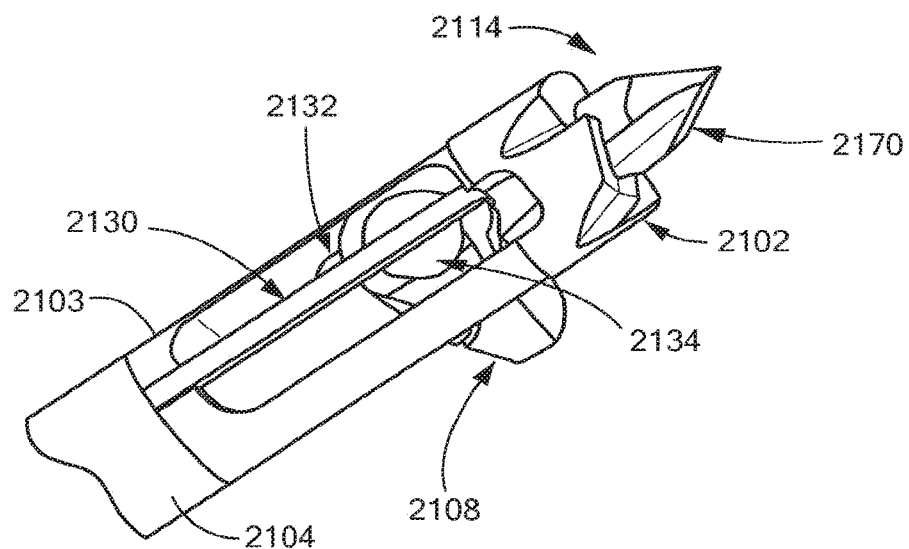
FIGS. 22d-22f illustrate are exemplary distal tip of the retro guidewire reamer of FIGS. 20a and 20b.

As shown in FIG. 22c, while the cutting member 2108 is being moved to its fully deployed position, the guidewire 2114 can twist within the tubular shaft 2103 and become engaged with and/or locked into the cutting member 2108. In one embodiment, the guidewire 2114 can include at least one helix spline 2170 (see FIGS. 20a, 22a, and 22c-22e), or any other suitable structural feature (e.g., a flute, a slot, a thread), configured to engage with and/or lock into the cutting member 2108 as the guidewire 2114 twists (or is twisted by a user) within the tubular shaft 2103. Once the cutting member 2108 is in its fully deployed position, the retro lock knob 2174 can be rotated (e.g., clockwise) to cause the pin or projection to engage the hole 2178 and make contact with the guidewire 2114 disposed in the tubular shaft 2103, thereby securing, stabilizing, and strengthening the guidewire 2114, the tubular shaft 2103, and the cutting member 2108 as a unit.

Figure 22E:
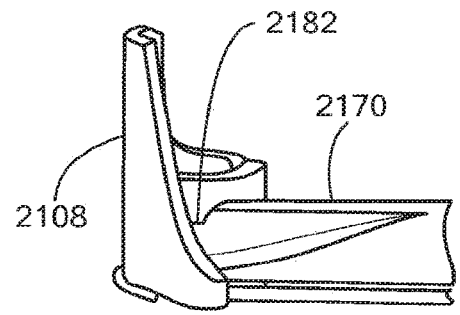
Figure 22F:
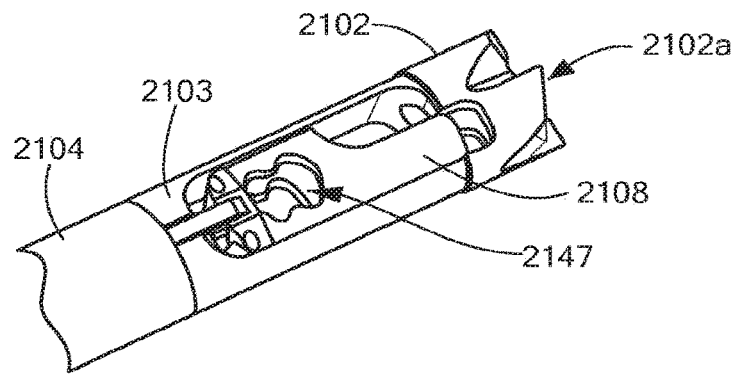

FIG. 22d depicts a detailed view of the drill bit 2102, the tubular shaft 2103, the outer tubular shaft 2104, and the cutting member 2108 in its fully deployed position. While the cutting member 2108 is in its fully deployed position, the helix spline 2170 (or any other suitable structural feature of the guidewire 2114) can engage with and/or lock into the cutting member 2108. In one embodiment, the helix spline 2170 can engage with and/or lock into a tab 2182 formed in the cutting member 2108, as shown in FIG. 22e. FIG. 22d further depicts the retrograde actuator 2130, as well as a lug configuration 2132, for use in conjunction with the retro drive bushing 2172 for deploying the cutting member 2108. FIG. 22d also depicts a hole 2134 through the cutting member 2108 that is adapted to accommodate the guidewire 2114 while the cutting member 2108 is in its closed position. FIG. 22f depicts a detailed view of the cutting member 2108 in its closed position, a plurality of flutes 2102a formed on the drill bit 2102, and a hole 2147 through the cutting member 2108 that is adapted to accommodate the guidewire 2114 while the cutting member 2108 is in its deployed (or opened) position. In one embodiment, the hole 2147 through the cutting member 2108 is adapted to receive the helix spline 2170 of the guidewire 2114, which, in conjunction with the retro lock knob 2174, can provide further support and stabilization to the cutting member 2108 in its deployed position, while securing the guidewire 2114, the tubular shaft 2103, and the cutting member 2108 as a unit.

Figure 23A:
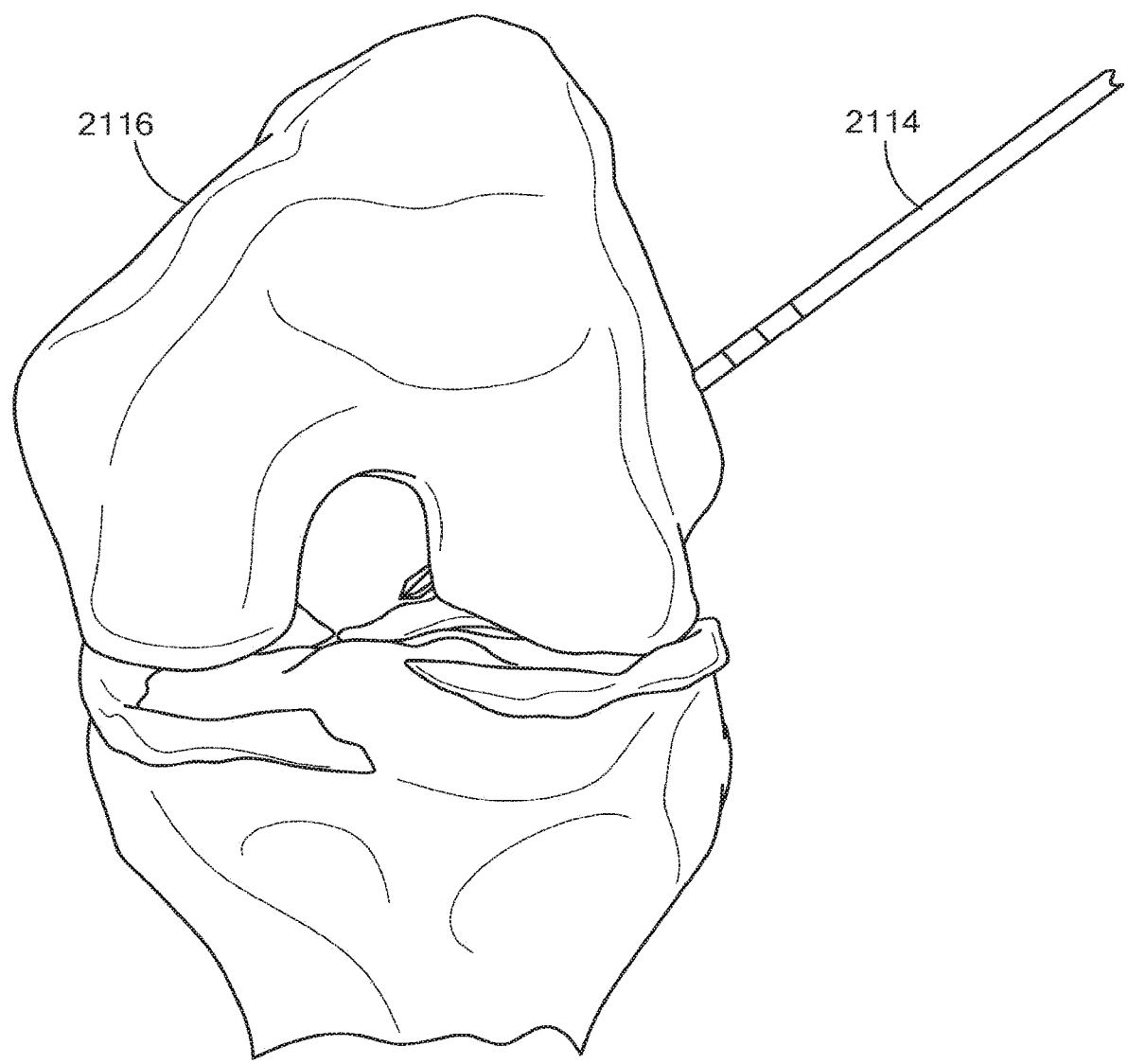
Figure 23C:
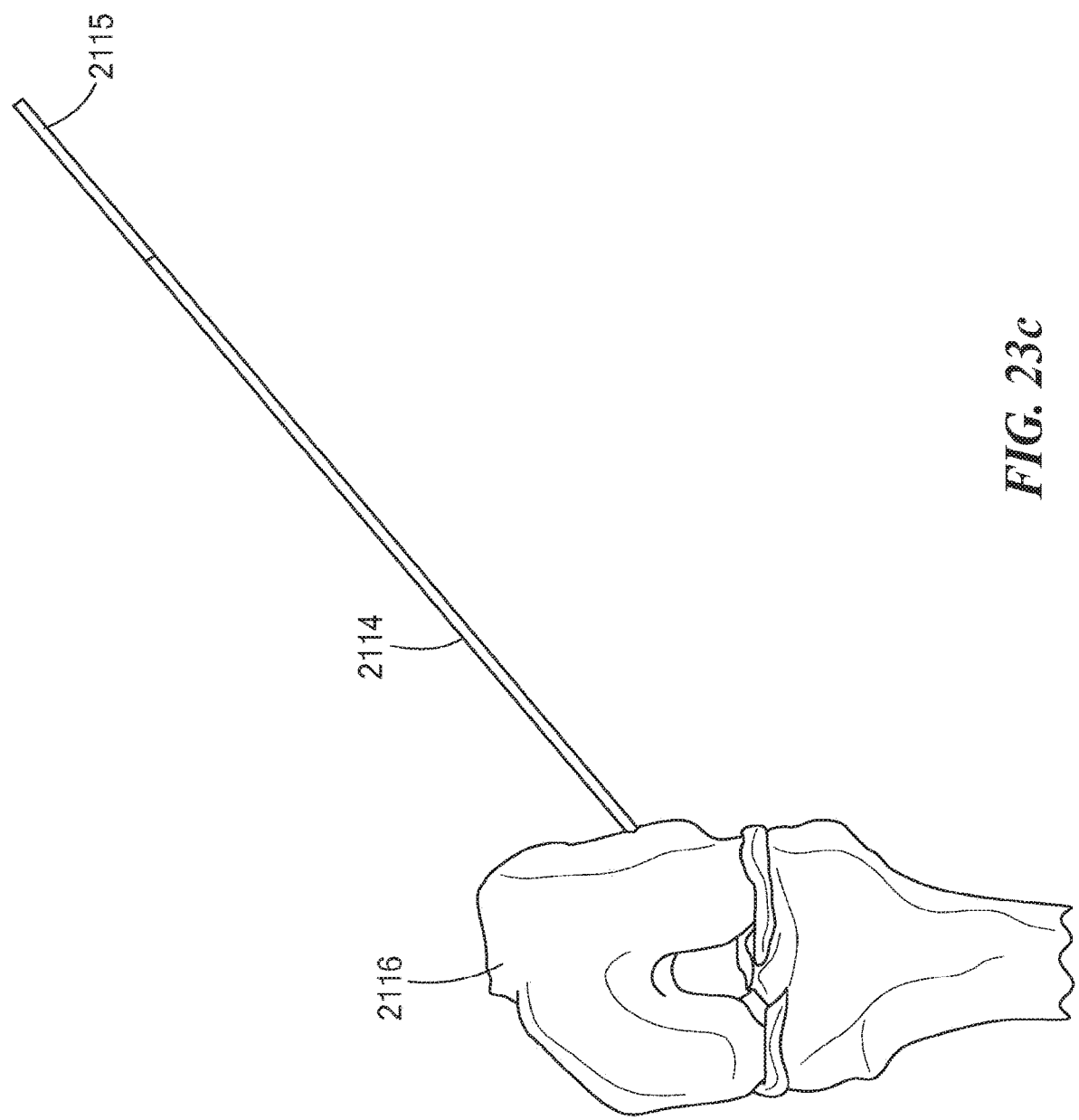
Figures 23D, 23E:
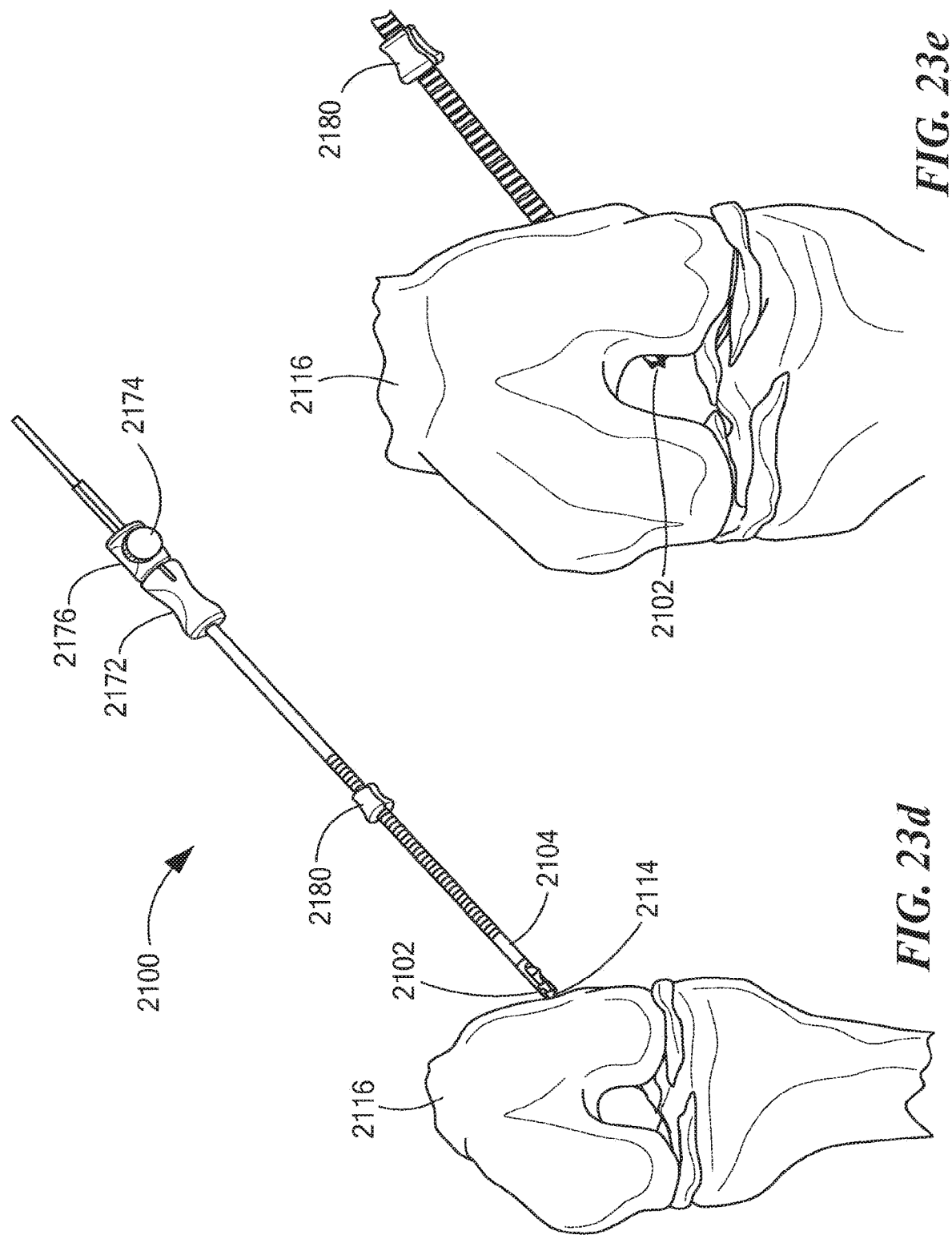
Figure 23H:
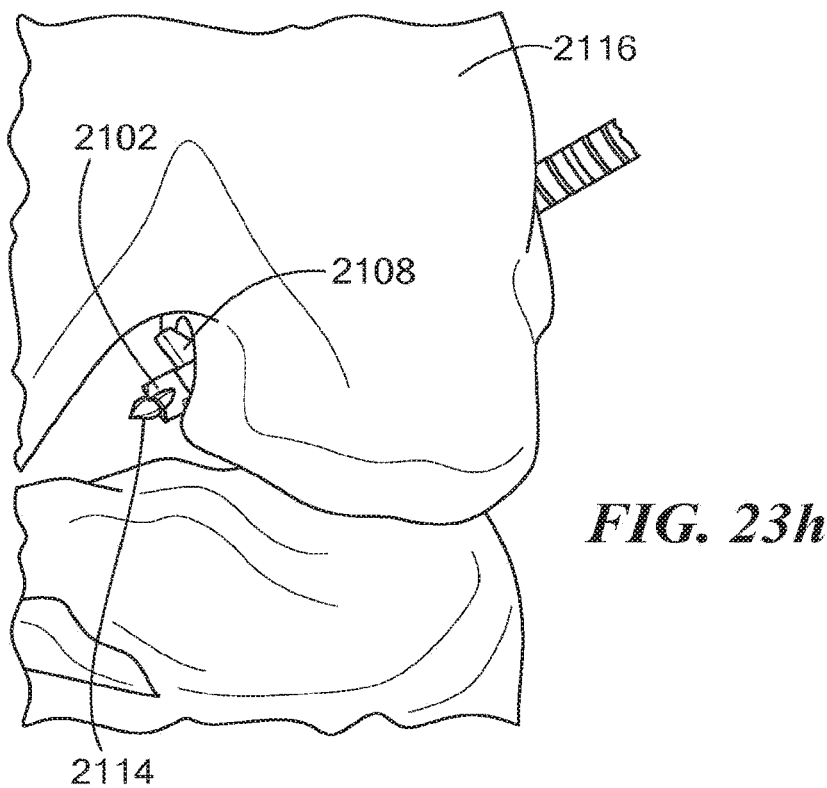
Figure 23I:
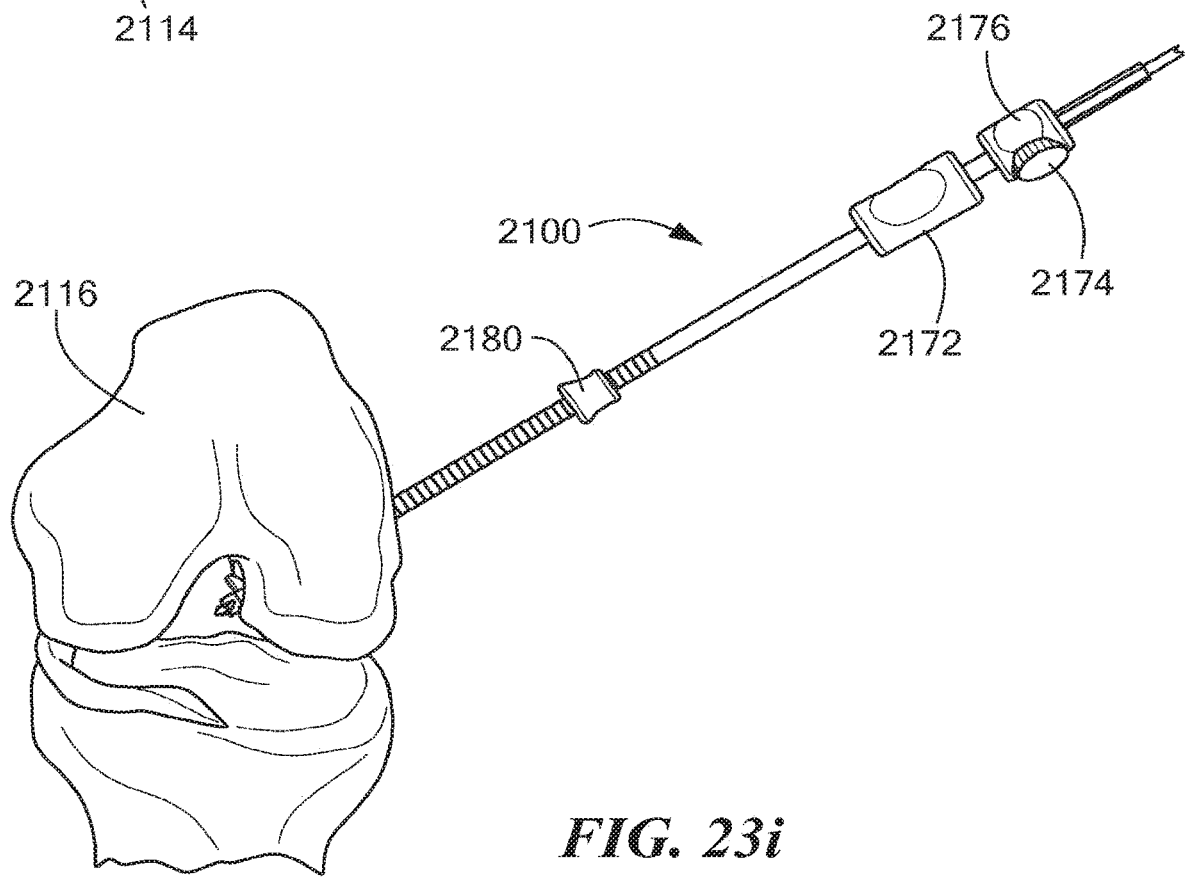

FIGS. 23a-23m illustrate an exemplary mode of operating the retro guidewire reamer 2100 of FIGS. 20a and 20b. In this mode of operation, a surgeon can use a guide (not shown) to establish a desired path for the guidewire 2114 through femoral bone 2116 (see FIG. 23a). For example, the guide may be a pinpoint guide, or any other suitable guide. The surgeon places the guidewire 2114 along the desired path and removes the guide. The surgeon then obtains a measure straw 2115 that is substantially the same length as the guidewire 2114 (see FIG. 23b). The surgeon places the measure straw 2115 against the femoral bone 2116, and cuts the measure straw 2115, as desired and/or required, at its proximal end (see FIG. 23c).

Next, the surgeon determines the size of a primary bone tunnel 2112 (see FIGS. 23k-23m), as well as the size of a counter bore 2110 (see FIGS. 23k-23m) through the femoral bone 2116 appropriate to fit a replacement tendon graft, using any suitable technique known in the art. Using the drill bit 2102 appropriately sized to create the primary bone tunnel 2112 (e.g., the drill bit 2102 can be a 4.5 mm drill bit or any other suitable drill bit), the surgeon uses a power drill (not shown) to drill the bone tunnel 2112 through the femoral bone 2116 over the guidewire 2114 from the outside in (see FIGS. 23d and 23e). The surgeon then at least partially retracts the guidewire 2114, and moves the retro drive bushing 2172 along the outer tubular shaft 2104 toward the distal end of the tubular shaft 2103, causing the retrograde actuator 2130 to move the cutting member 2108 to its deployed position (see FIGS. 23f and 23g). While the cutting member 2108 is being moved to its fully deployed position, the guidewire 2114 twists within the tubular shaft 2103 as the helix spline 2170 becomes engaged with and/or locks into the tab 2182 (see FIG. 22e) of the cutting member 2108 (see FIG. 23h). Once the cutting member 2108 is in its fully deployed position, the surgeon rotates (e.g., clockwise) the retro lock knob 2174 to secure and stabilize the guidewire 2114, the tubular shaft 2103, and the cutting member 2108 together as a unit (see FIG. 23i).

Figure 23J:
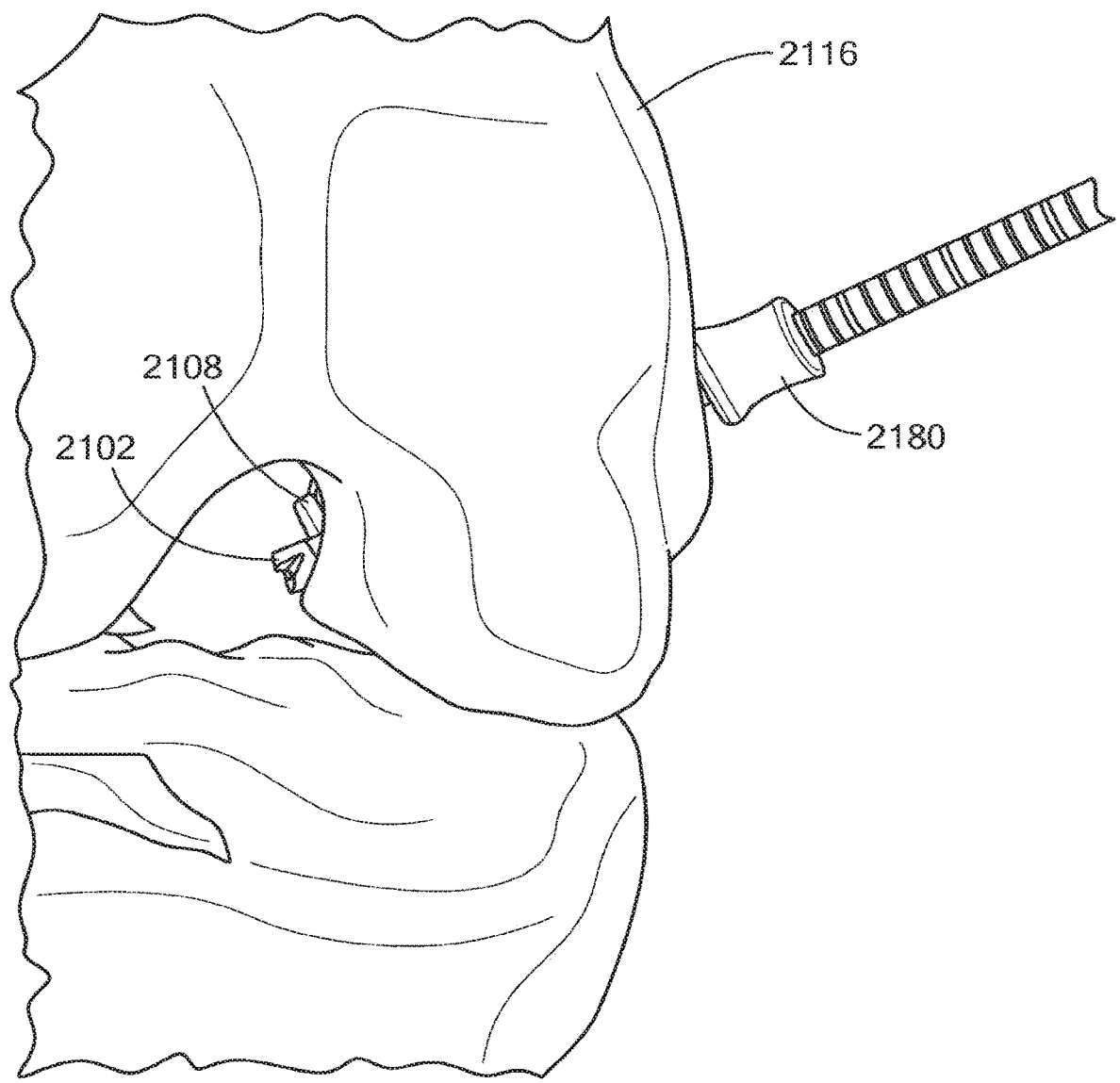
Figure 23K:
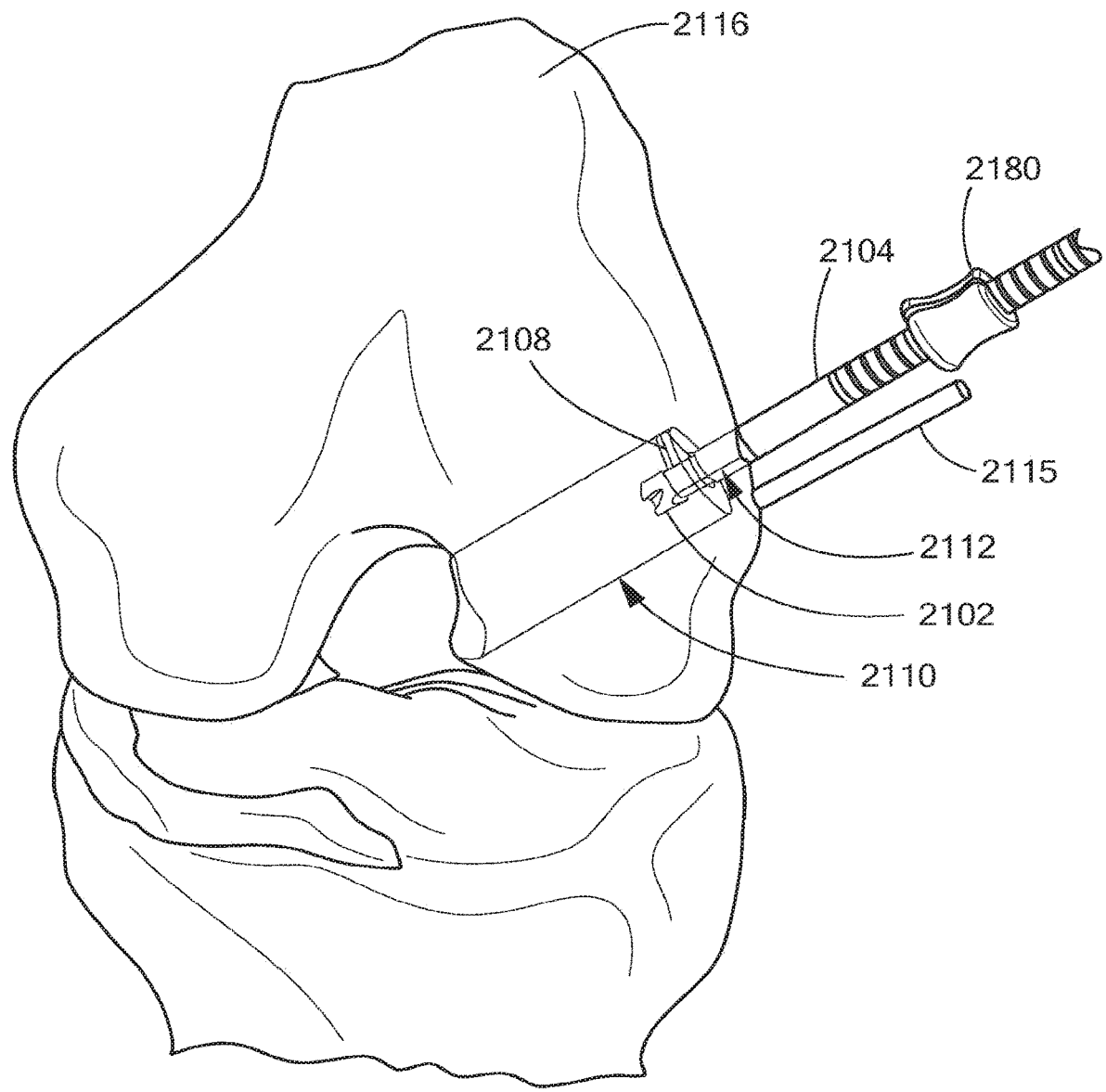
Figures 23L, 23M:
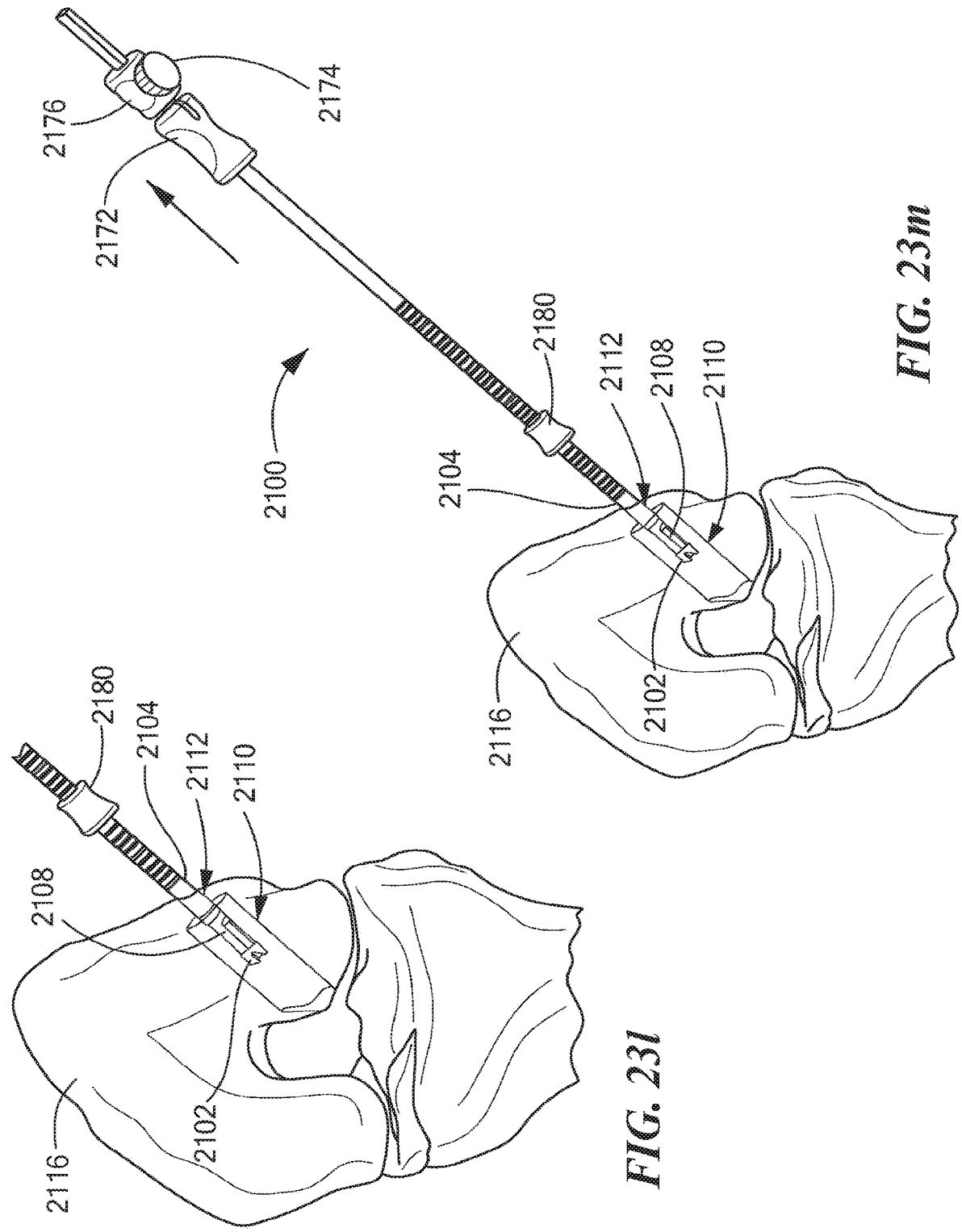

Next, the surgeon places the depth slide 2180 against a lateral side of the femoral bone 2116 to determine the length of the counter bore 2110 (see FIG. 23j). Alternatively, instead of the depth slide 2180, a depth straw (not shown) may be employed for determining the length of the counter bore 2110. The surgeon then uses the power drill with the deployed cutting member 2108 to create the counter bore 2110 through the femoral bone 2116 in a retrograde manner (see FIG. 23k). Once the counter bore 2110 is drilled, the surgeon rotates (e.g., counter clockwise) the retro lock knob 2174 to release the guidewire 2114 from within the tubular shaft 2103, untwists the guidewire 2114 within the tubular shaft 2103 to disengage the helix spline 2170 from the cutting member 2108, and moves the retro drive bushing 2172 along the outer tubular shaft 2104 toward the retro lock knob 2174 to cause the retrograde actuator 2130 to move the cutting member 2108 from its deployed (opened) position to its closed position, allowing the retro guidewire reamer 2100 to be withdrawn through the primary bone tunnel 2112 created by the drill bit 2102 (see FIGS. 23l and 23m).

It is noted that, in the exemplary mode of operation described above, the counter bore 2110 may be drilled along the axis of the primary bone tunnel 2112, or at a predetermined angle to the primary bone tunnel axis. It is further noted that the retro guidewire reamer 2100 is cannulated to allow fluid to pass through the tubular shaft 2103 and/or the outer tubular shaft 2104 during use, thereby clearing out any soft tissue that may potentially block the deployment of the cutting member 2108.

Having described the above exemplary embodiment of the retro guidewire reamer 2100, other alternative embodiments or variations may be made. For example, the bone tunnel 2112 may be drilled through the femoral bone 2116 over the guidewire 2114 with the distal tip of the retro guidewire reamer 2100 enclosed. The counter bore 2110 may then be drilled after pivoting, rotating, or otherwise moving the cutting member 2108 to its deployed position.

Figure 24:
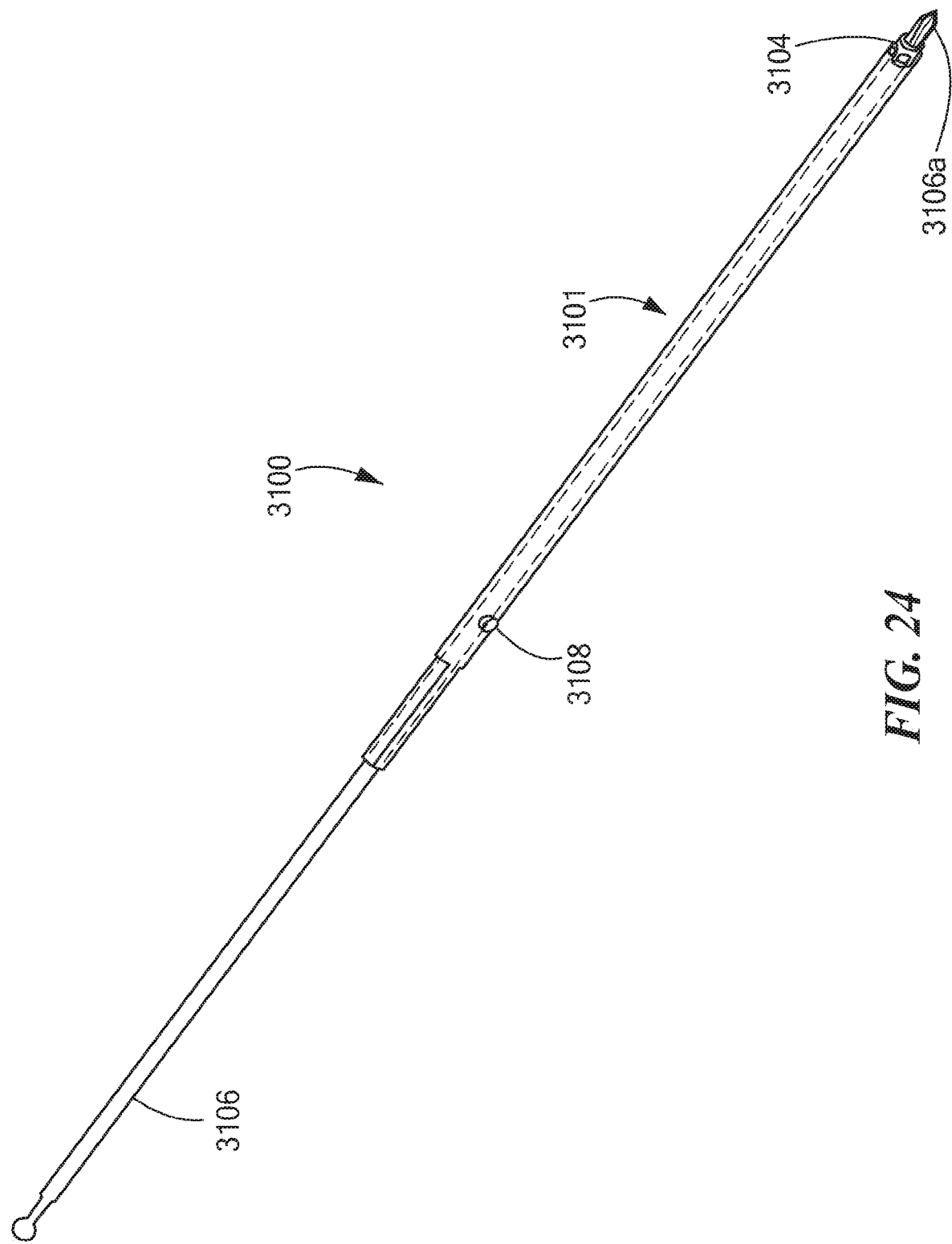
FIG. 24 illustrates a third alternative embodiment of the retro guidewire reamer of FIGS. 6a and 6b.

FIG. 24 depicts another illustrative embodiment of an exemplary retro guidewire reamer 3100 for creating tunnels through bone tissue during arthroscopic ligament reconstruction surgery, in accordance with the present application. As shown in FIG. 24, the retro guidewire reamer 3100 includes a drill bit 3101 having a tubular (cannulated) shaft 3102, and a cutting member 3104 configured as a small hollow segment. The cutting member 3104 is pivotally, rotatably, or otherwise movably coupled at a distal end of the cannulated shaft 3102. The retro guidewire reamer 3100 is operative to drill a tunnel through bone over a guidewire 3106 in an antegrade manner, and to drill a counter bore through the bone over the guidewire 3106 in a retrograde manner. The retro guidewire reamer 3100 further includes a lock screw 3108 for locking the guidewire 3106 in place, as needed, during use. As further shown in FIG. 24, the guidewire 3106 can have a pointed distal end 3106a.

Figure 25:
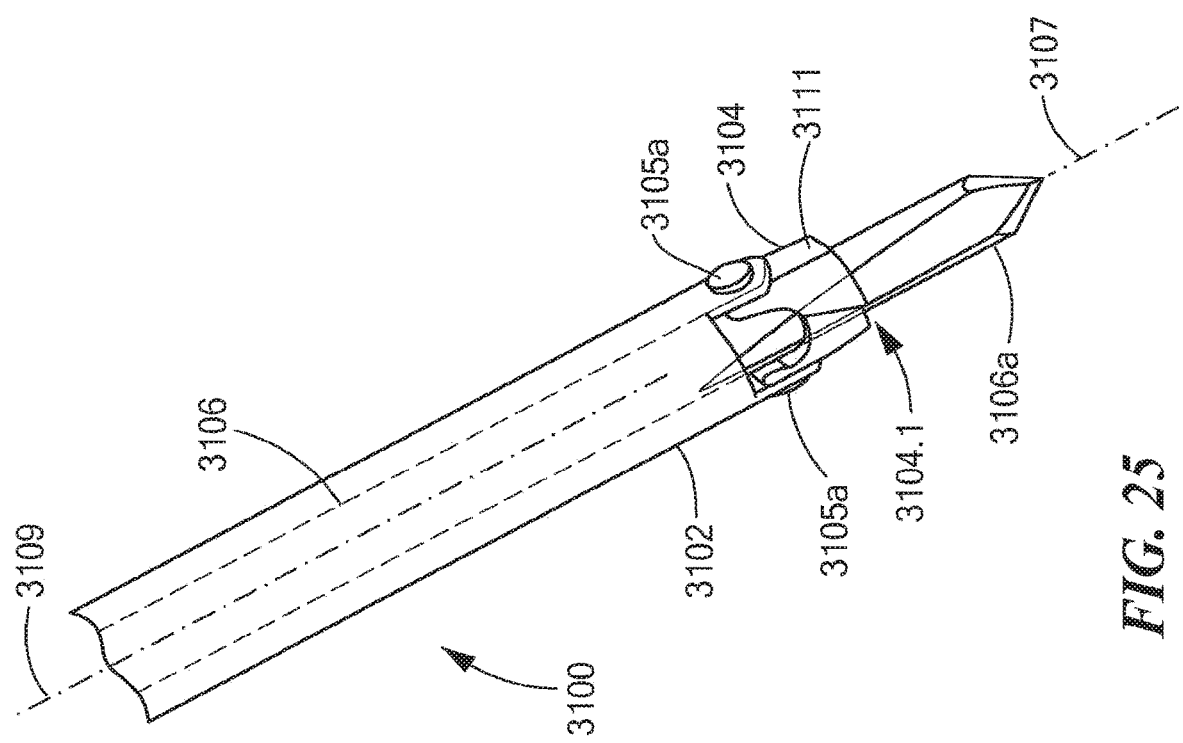
FIG. 25 illustrates a detailed view of the retro guidewire reamer of FIG. 24 in a configuration for drilling a tunnel through bone tissue over a guidewire in an antegrade manner.

FIG. 25 depicts a detailed view of the retro guidewire reamer 3100 of FIG. 24 in a configuration for drilling a tunnel through bone over the guidewire 3106 in an antegrade manner. As shown in FIG. 25, the cutting member 3104 is pivotally coupled, by a pair of pivot pins 3105a at a distal end of the cannulated shaft 3102 in a first position where its central axis 3107 is coincident with the longitudinal axis 3109 of the shaft 3102. The cutting member 3104 has a tubular (cannulated) sidewall 3111 with sharpened edges 3104.1 at a forward circumferential end thereof.

Figure 26:
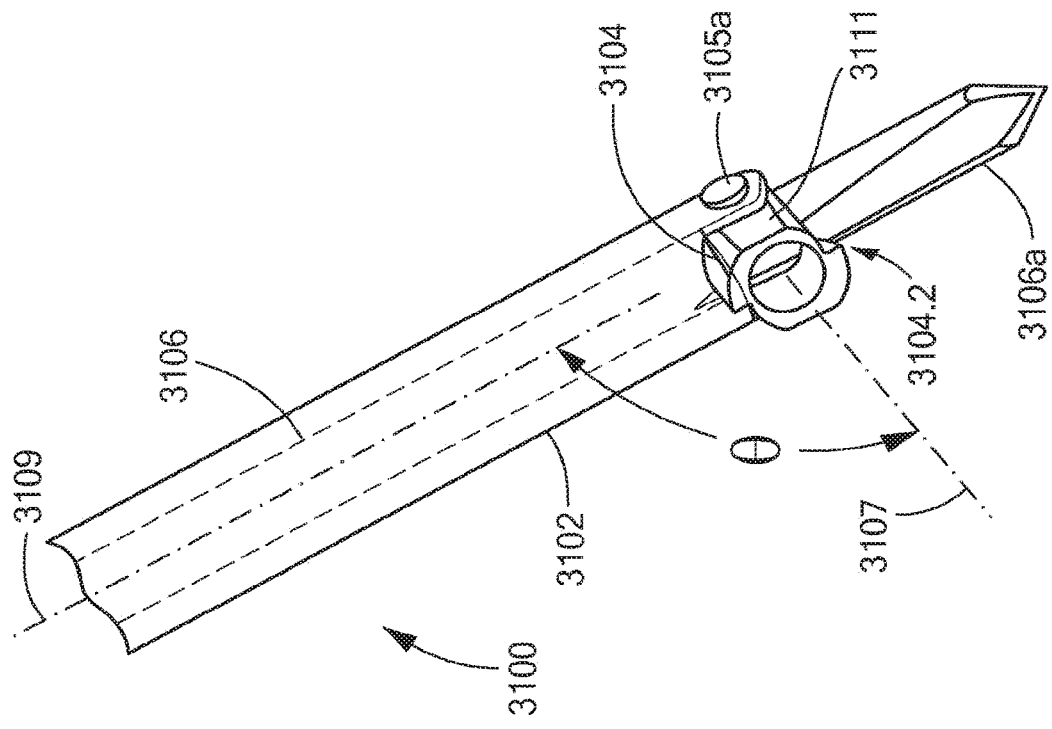
FIG. 26 illustrates a detailed view of the retro guidewire reamer of FIG. 24 in a configuration for drilling a counter bore through bone tissue over a guidewire in a retrograde manner.

FIG. 26 is another detailed view of the retro guidewire reamer 3100 of FIG. 24 in a configuration for drilling a counter bore through bone over the guidewire 3106 in a retrograde manner. As shown in FIG. 26, the cutting member 3104 is pivotally, rotatably, or otherwise movably coupled at the distal end of the cannulated shaft 3102 such that it can pivot, rotate, or otherwise move from the first position where its central axis 3107 was coincident with the longitudinal axis 3109 of the shaft 3102 (see FIG. 25), to a second position where its central axis 3107 is disposed at an angle θ to the longitudinal axis 3109 of the shaft 3102. The cannulated sidewall 3111 of the cutting member 3104 also has sharpened edges 3104.2 on an outside surface thereof.

The disclosed retro guidewire reamer 3100 will be further understood with reference to the following illustrative example, and FIGS. 27-31. In this example, the retro guidewire reamer 3100 is employed in an arthroscopic surgical procedure to drill a tunnel 3402 (see FIG. 27) through femoral bone 3400 over the guidewire 3106 in an antegrade manner, and to drill a counter bore 3802 (see FIG. 30) through the femoral bone 3400 over the guidewire 3106 in a retrograde manner. First, a surgeon establishes a desired path 3401 through the femoral bone 3400 for the guidewire 3106 using a guide (not shown), places the guidewire 3106 along the path 3401, and removes the guide. With the cannulated shaft 3102 and the cutting member 3104 in the first position (see FIG. 25) placed over the guidewire 3106, the surgeon uses the retro guidewire reamer 3100 to drill the tunnel 3402 through the femoral bone 3400 over the guidewire 3106 from the outside in, in an antegrade manner. In this example, the surgeon drills the bone tunnel 3402 using the sharpened edges 3104.1 at the forward circumferential end of the cutting member 3104.

Figure 28:
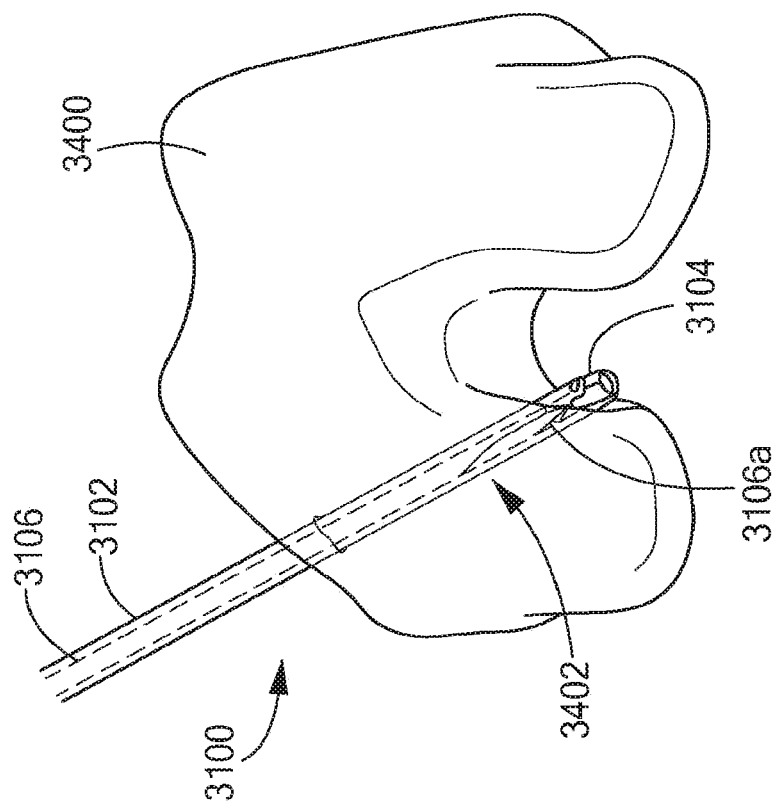
FIGS. 27-31 illustrate an exemplary use of the retro guidewire reamer of FIG. 24 for creating a tunnel and a counter bore through femoral bone tissue.
Figure 27:
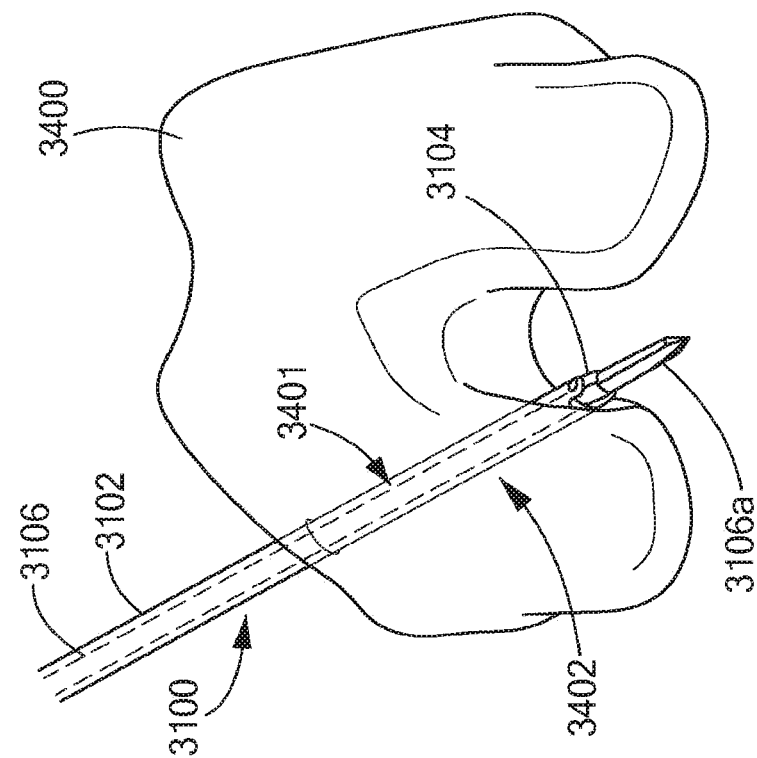
Figure 30:
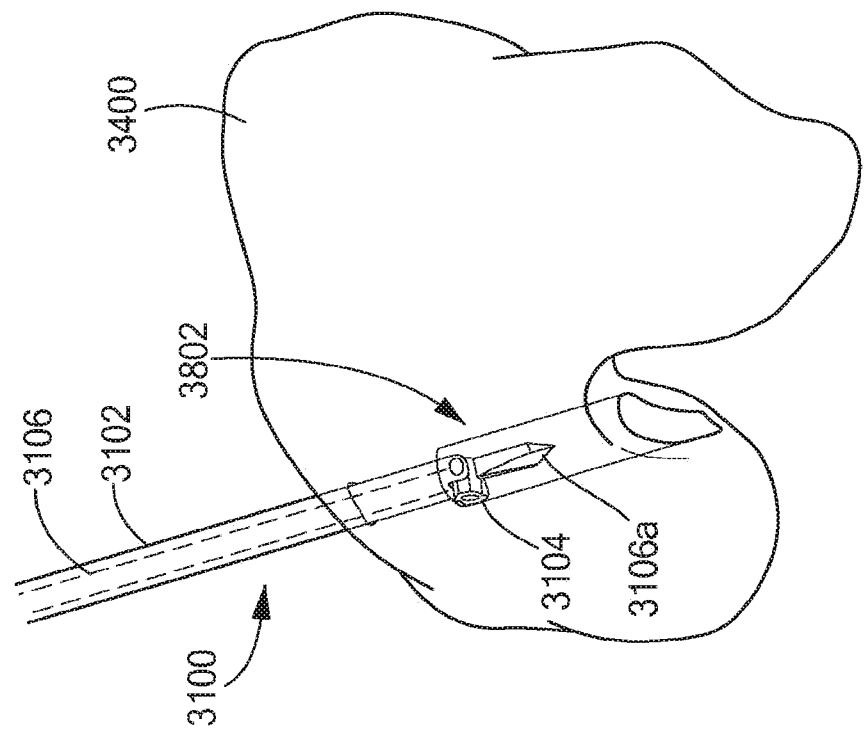
Figure 29:
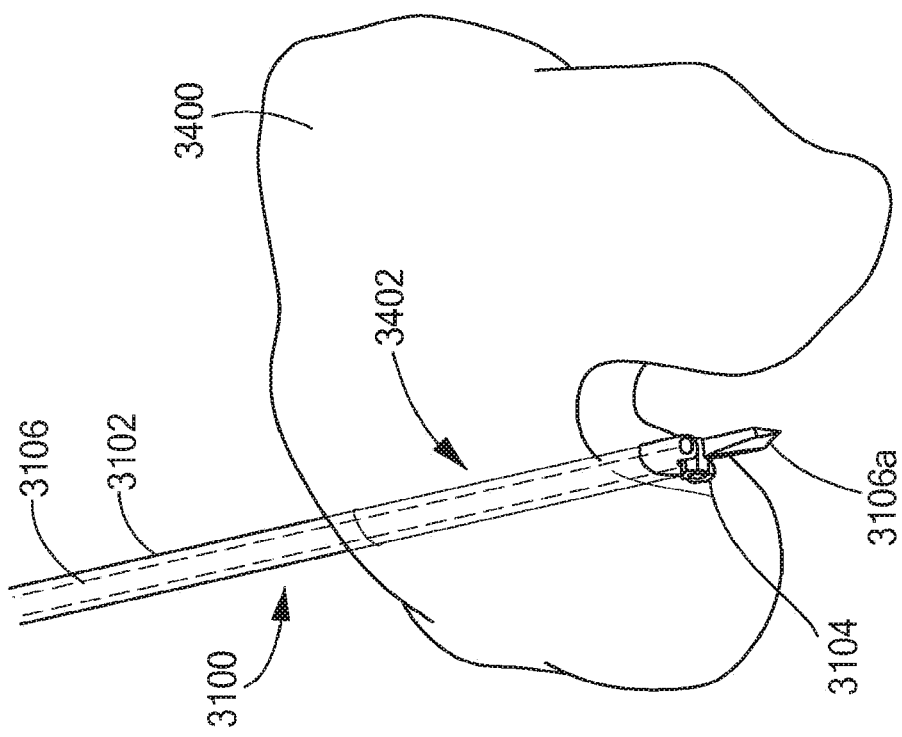
Figure 31:
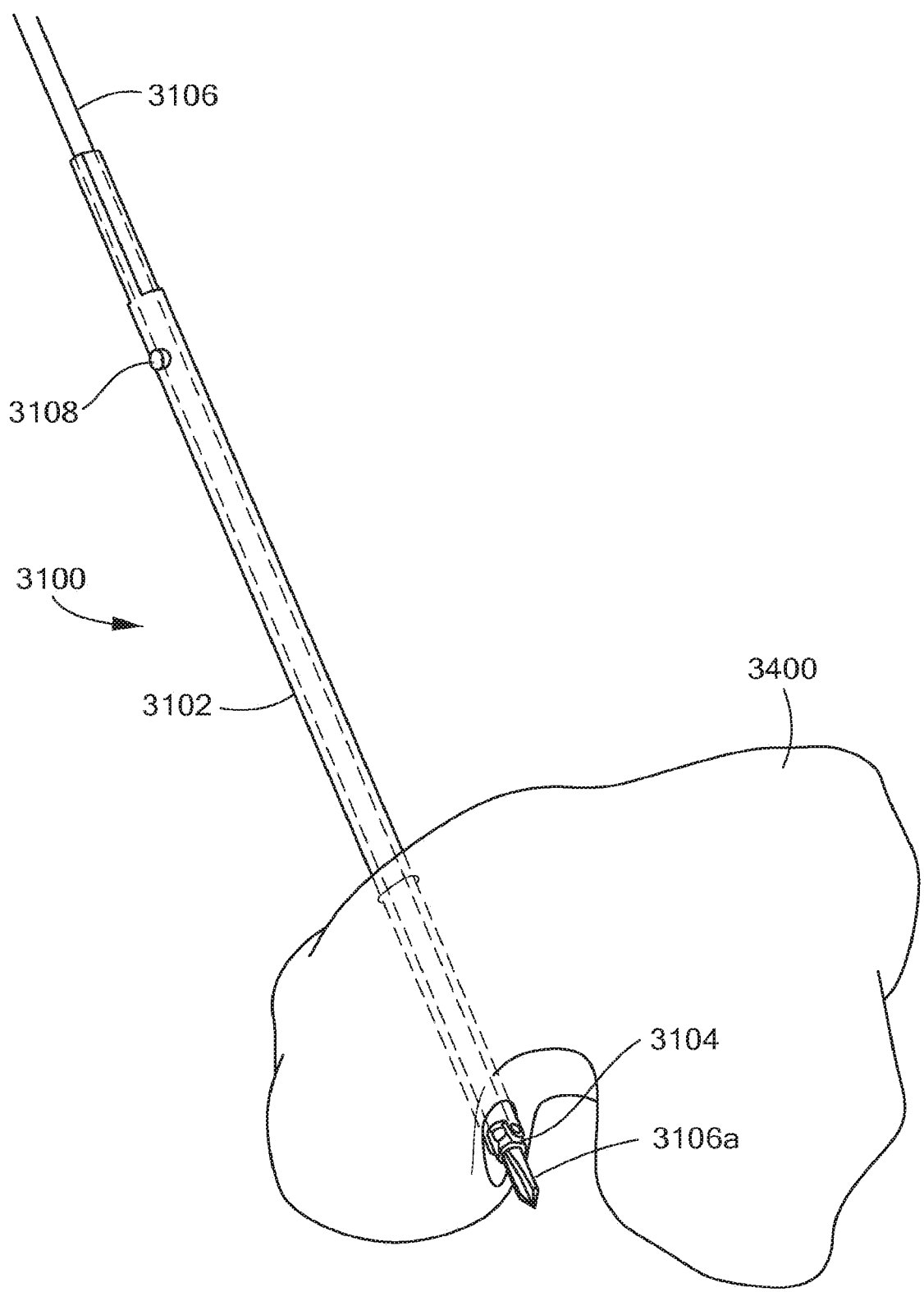

Next, the surgeon retracts the guidewire 3106, causing its pointed distal end 3106a to be withdrawn inside the cannulated shaft 3102 so that it is no longer engaged with the cutting member 3104 and blocking or otherwise preventing the cutting member 3104 from movement (see FIG. 28). Such retraction of the guidewire 3106 allows the cutting member 3104 to pivot, rotate, or otherwise move from the first posit on where its central axis 3107 was coincident with the shafts longitudinal axis 3109 (see FIG. 25), to the second position where its central axis 3107 is disposed at the angle θ to the shaft's longitudinal axis 3109 (see FIGS. 26 and 29). The surgeon then advances the guidewire 3106, causing pointed distal end 3106a to pass through the cannulated shaft 3102 to a position beyond the pivot coupling of the cutting member 3104 and the shaft 3102, and to block or otherwise prevent any further movement of the cutting member 3104 (see FIG. 29). The surgeon can now lock the guidewire 3106 to the cannulated shaft 3102 using the lock screw 3108 (see FIG. 31), thereby securing the cutting member 3104 in the angled second position. With the cannulated shaft 3102 placed over the guidewire 3106 and the cutting member 3104 in the second position, the surgeon can drill the counter bore 3802 (see FIG. 30) through the femoral bone 3400 over the guidewire 3106 in a retrograde manner, using the sharpened edges 3104.2 on the outside surface of the cutting member's sidewall 3111.

Having described the above exemplary embodiment of the disclosed retro guidewire reamer 3100, other alternative embodiments or variations may be made. For example, it was described herein that a surgeon can drill a bone tunnel over the guidewire 3106 in an antegrade manner using the sharpened edges 3104.1 at the forward circumferential end of the cutting member 3104, and drill a counter bore through the bone over the guidewire 3106 in a retrograde manner using the sharpened edges 3104.2 on the outside surface of the cutting member's sidewall 3111. In an alternative embodiment 3900 of the retro guidewire reamer (see FIG. 32) sharpened edges at a forward circumferential end of a tubular (cannulated) shaft 3902 can be used to drill a bone tunnel over a guidewire in an antegrade manner.

Figure 32:
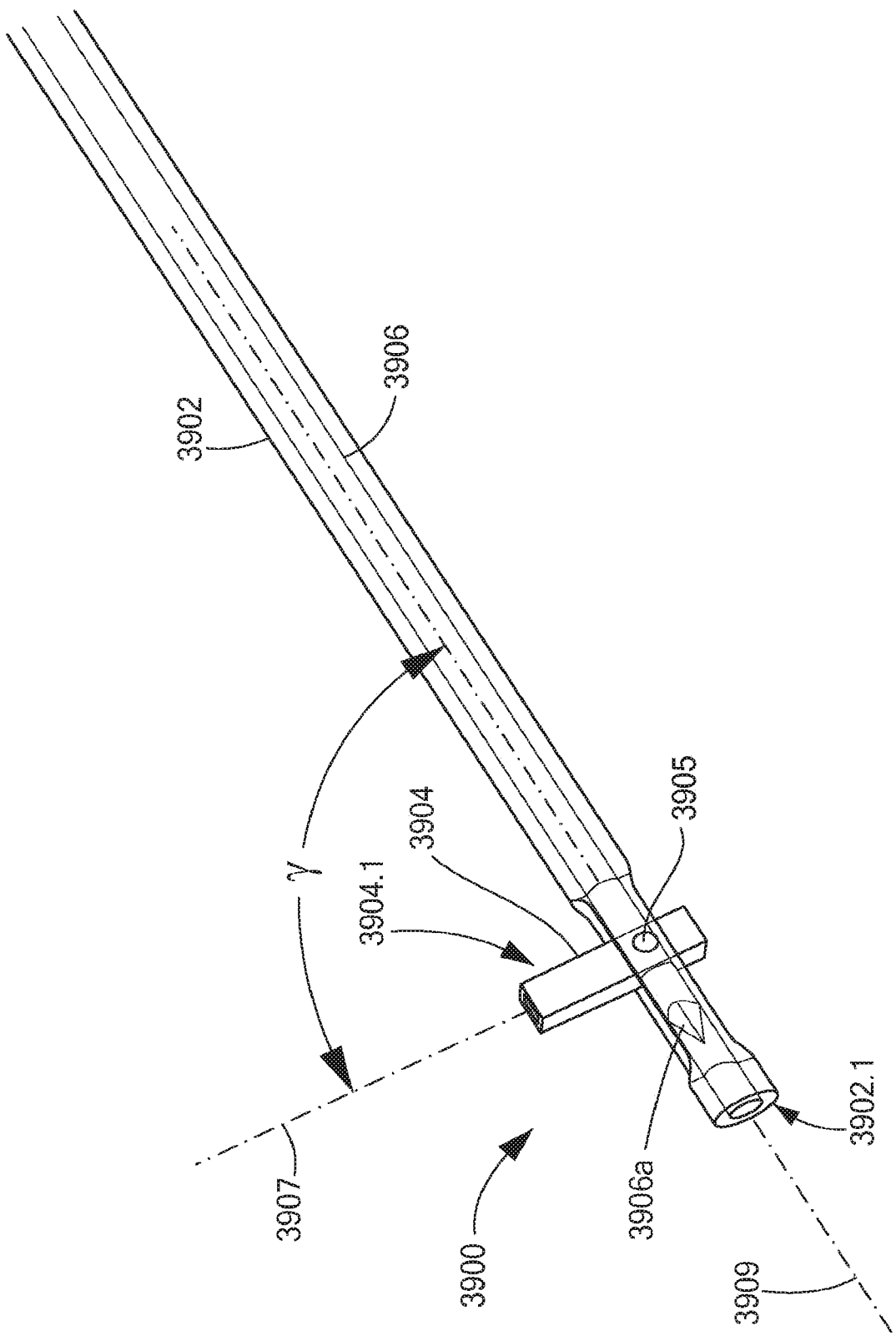
FIG. 32 illustrates an alternative embodiment of the retro guidewire reamer of FIG. 24.

FIG. 32 depicts the retro guidewire reamer 3900, which includes a drill bit having the cannulated shaft 3902 with a longitudinal axis 3909, and a cutting member 3904 configured as a small hollow segment with a central axis 3907. The cutting member 3904 is pivotally coupled by pivot pins 3905 adjacent a distal end of the cannulated shaft 3902 such that it can rotate from a first position where its central axis 3907 is coincident with the longitudinal axis 3909 of the shaft 3902, to a second position where its central axis 3907 is disposed at an angle γ to the longitudinal axis 3909 of the shaft 3902. The cannulated shaft 3902 has sharpened edges 3902.1 at a forward circumferential end thereof for drilling a bone tunnel over a guidewire 3906 in an antegrade manner, and the cutting member 3904 has a sidewall with sharpened edges 3904.1 on an outside surface thereof for drilling, a counter bore over the guidewire 3906 in a retrograde manner.

It is noted that, after the cutting member 3904 is rotated to the second position where its central axis 3907 is disposed at the angle γ to the longitudinal axis 3909 of the shaft 3902, a surgeon can advance the guidewire 3906, causing its pointed distal end 3906a to pass through the cannulated shaft 3902 to a position beyond the pivot coupling of the cutting member 3904 and the shaft 3902, and to block or otherwise prevent any further rotation or movement of the cutting member 3904 (see FIG. 32). An opening is provided in the portion of the cutting member's sidewall disposed within the cannulated shaft 3902 to allow the pointed distal end 3906a of the guidewire 3906 to pass through the cutting member 3904 when it is disposed in the second position (see FIG. 32). To allow the cutting member 3904 to pivot, rotate, or otherwise move from the second position back to the first position, where its central axis 3997 is coincident with the longitudinal axis 3909 of the shaft, the surgeon can retract the guidewire 3906, causing its pointed distal end 3906a to be withdrawn inside the cannulated shaft 3902 so that it is no longer engaged with the cutting member 3904 and blocking or otherwise preventing the cutting member 3904 from rotation or movement.

Figure 33:
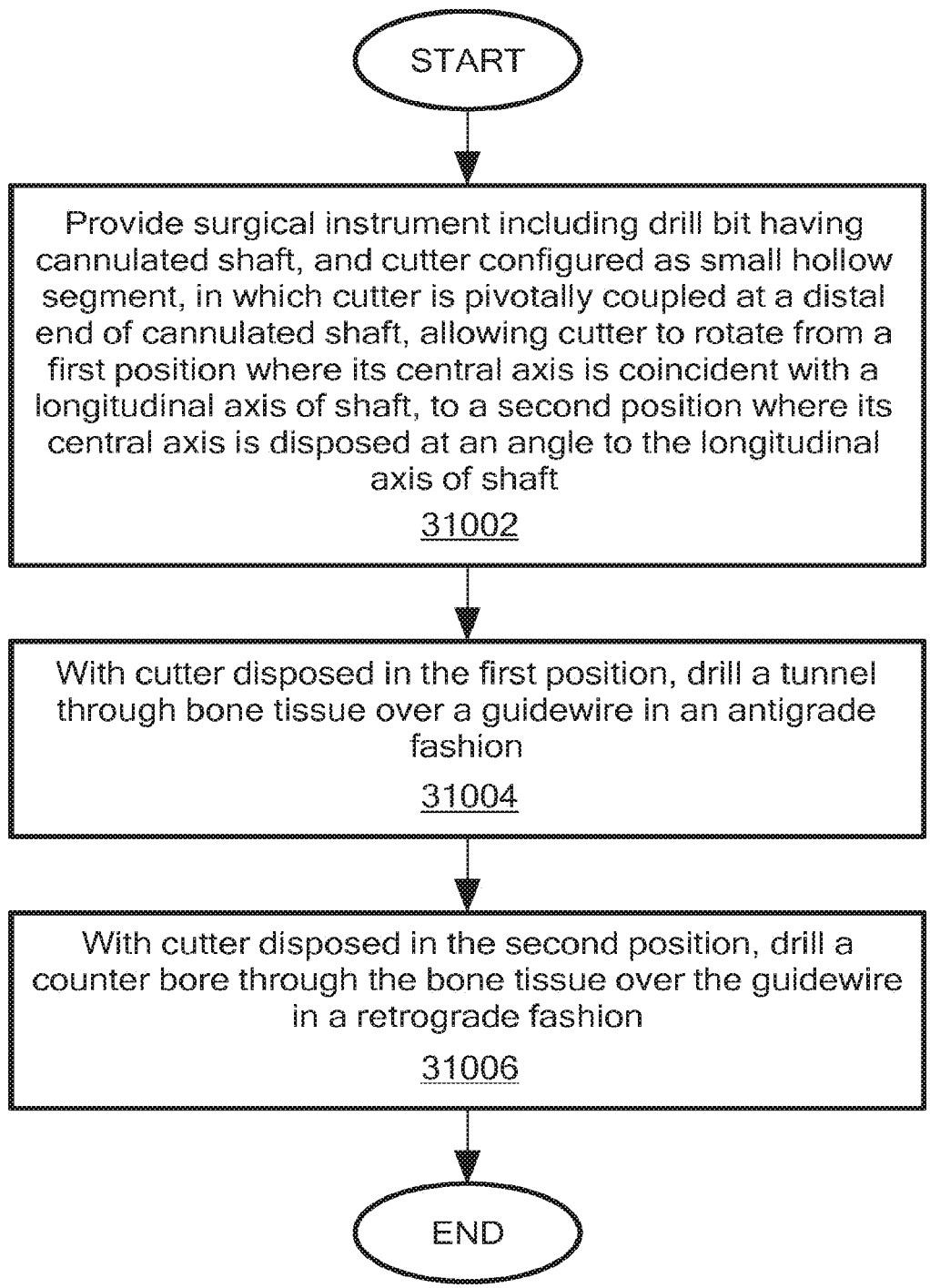
FIG. 33 is a flow diagram illustrating an exemplary method of operating the retro guidewire reamer of FIG. 24.

A method of operating the disclosed retro guidewire reamers 3100, 3900 for creating tunnels through bone tissue during arthroscopic ligament reconstruction surgery is described below with reference to FIG. 33. As depicted in block 31002, a retro guidewire reamer is provided including a drill bit having a cannulated shaft, and a cutting member configured as a small hollow segment, in which the cutting member is pivotally, rotatably or otherwise movably coupled at a distal end of the cannulated shaft, allowing the cutting member to pivot, rotate, or otherwise move from a first position where its central axis is coincident with a longitudinal axis the shaft, to a second position where its central axis is disposed at an angle to the longitudinal of the shaft. As depicted in block 31004, with the cutting member disposed in the first position, a tunnel is drilled through the bone over a guidewire in an antegrade manner. As depicted in block 31006, with the cutting member disposed in the second position, a counter bore is drilled through the bone over the guidewire in a retrograde manner.

It will be appreciated by those of ordinary skill in the art that modifications to and variations of the above-described apparatus and methods may be made without departing from the inventive concepts disclosed herein. Accordingly, the invention should not be viewed as limited except as by the scope and spirit of the appended claims.

What is claimed is:

1. A method of performing an arthroscopic surgical procedure, comprising:
    disposing a surgical instrument including a cannulated shaft over a guidewire, the surgical instrument further including:
        a cutting member movably disposed adjacent a distal end of the cannulated shaft, the cutting member being configured to move between a closed position where a central axis thereof is coincident with a longitudinal axis of the cannulated shaft, and a deployed position where the central axis of the cutting member is disposed at an angle to the longitudinal axis of the cannulated shaft; and
        a drive bushing configured for axial movement along an outer surface of the cannulated shaft for moving the cutting member between the closed position and the open position;
    while the cutting member is in the closed position, drilling a tunnel through bone over the guidewire in an antegrade manner;
    using the drive bushing, moving the cutting member from the closed position to the deployed position; and
    while the cutting member is in the deployed position:
        engaging the cutting member with the guidewire to prevent movement of the cutting member from the deployed position; and
        drilling, by the cutting member, a counter bore through the bone over the guidewire in a retrograde manner.

2. The method of claim 1 wherein the cutting member has a cannulated sidewall with sharpened edges at a forward circumferential end thereof, and wherein the drilling of the tunnel includes drilling the tunnel through the bone over the guidewire using the sharpened edges at the forward circumferential end of the cannulated sidewall of the cutting member.

3. The method of claim 1 wherein the cutting member has a cannulated sidewall with sharpened edges on an outside surface thereof, and wherein the drilling of the counter bore includes drilling the counter bore through the bone over the guidewire using the sharpened edges on the outside surface of the cannulated sidewall.

4. The method of claim 1 further comprising:
    while the cutting member is in the closed position, retracting the guidewire within the cannulated shaft to allow the cutting member to move from the closed position where its central axis is coincident with the longitudinal axis of the cannulated shaft, to the deployed position where its central axis is disposed at the angle to the longitudinal axis of the cannulated shaft.

5. The method of claim 1 further comprising:
    while the cutting member is in the deployed position, advancing the guidewire within the cannulated shaft to prevent movement of the cutting member from the deployed position during use.

6. The method of claim 1 wherein said drilling the tunnel through bone over the guidewire in an antegrade manner comprises drilling the tunnel with the distal end of the cannulated shaft, the distal end of the cannulated shaft comprising a drill bit.

7. The method of claim 1 further comprising securing the guidewire within the cannulated shaft with a locking mechanism, the locking mechanism being included in the drive bushing.

8. The method of claim 1 wherein the at least one cutting member defines a hole through the cutting member adapted to accommodate passage of the guidewire therethrough least while in the deployed position.

9. The method of claim 8 wherein the hole is configured to be engageable with a structural feature of the guidewire while in the deployed position.

\* \* \* \* \*